US005549974A

United States Patent [19]

Holmes

[11] Patent Number: 5,549,974
[45] Date of Patent: Aug. 27, 1996

[54] METHODS FOR THE SOLID PHASE SYNTHESIS OF THIAZOLIDINONES, METATHIAZANONES, AND DERIVATIVES THEREOF

[75] Inventor: Christopher P. Holmes, Sunnyvale, Calif.

[73] Assignee: AFFYMAX Technologies NV, Curacao, Netherlands Antilles

[21] Appl. No.: 265,090

[22] Filed: Jun. 23, 1994

[51] Int. Cl.$^6$ .................... C07D 279/06; C07D 277/10; B32B 15/04; B32B 17/06
[52] U.S. Cl. .................... 428/403; 428/406; 428/407; 428/411.1; 428/426; 428/457; 544/54; 548/182
[58] Field of Search ............................ 548/182; 544/54; 428/403, 406, 407, 411.1, 426, 457

[56] References Cited

U.S. PATENT DOCUMENTS 4,225,609  9/1980  Cragoe et al. .................... 424/270
5,061,720  10/1991  Walsh et al. .................... 514/369

OTHER PUBLICATIONS

Hogale et al., Jul. 1991, Indian J. Chem. Sec. B. 717–720 Publication month not provided. Synthesis and antimicrobial activity of N10–arylidenehydrazoidophenothiazine and their 4–thiazolidinones and 2–azetidinones.
El–Zohry., 1992, Oppi Briefs 24(1): 81–83 Publication month not provided. One–pot synthesis of 2–spirothiazolidin–4–one derivatives.
Surrey et al., 1954, J. Am. Chem. Sci., 76: 578–580 Publication month not provided. 4–Thiazolidones. VI The preparation of some 2–substituted derivatives.
Tanabe et al., 1991, Tetrahedron Letters 32(3): 383–386 Publication month not provided. Steroselective synthesis of anti–paf active thiazolidin–4–ones via cyclo–condensation of alkyl alpha–mercaptocarboxylates with arylimines.
Tanabe et al., 1991, Tetrahedron Letters 32(3): 379–382 Publication month not provided. Structure activity relationship of optically active 2–(3–pyridyl) thiazolidin–4–ones as a paf antagonist.

Diurno et al., 1992, J. Med. Chem. 35: 2910–2912 Publication month not provided. Synthesis and antihistaminic activity of some thiazolidin–4–ones.
Fuchigami et al., 1992, J. Org. Chem. 57: 3755–3757 Publication month not provided. Electrolytic partial fluorination of organic compounds. 4 Regioselective anodic monofluorination of 4–thiazolidinones and its application to the synthesis of monofluoro b–Lactams.
Abdel–Rahman et al., 1990, J. Indian Chem. 67: 61–64 Publication month not provided. Biologically active thiazolidinone. Part–1. Synthesis and fungitoxicities of thiazolidinones and their derivatives derived from ortho–Aminothiophenol.
Srivastava et al., 1991, Indian J. Chem. 30B: 620–623 Publication month not provided. Synthesis and fungitoxity of some 1,3,4– thiadiazolo (3,2–a) immidazoles and 3–(1, 3,4–thiadiazole–2–yl)–4–thiazolidinones.
Harhash et al., 1973, Indian J. of Chem., 11: 128–130 Publication month not provided. Reactions with Beta–aryl–1–Alpha–mercaptoacrylic acids: Part I–Synthesis of some heterocyclic sulphur compounds.
Katritzky, A. R. et al., *Handbook of Heterocyclic Chemistry* (Pergamon Press, Oxford), pp. 148, 151, 298, 307 (1985).
Gilchrist, T. L. *Adv. Heterocy. Chem..* 41, 41 (1987).

*Primary Examiner*—Philip I. Datlow
*Assistant Examiner*—King Lit Wong
*Attorney, Agent, or Firm*—Lauren L. Stevens

[57] ABSTRACT

The invention provides an efficient and versatile method for the combinatorial synthesis and screening of libraries of 4-thiazolidinones, metathiazanones, and derivatives thereof. In order to expediently synthesize a combinatorial library of derivatives based upon these core structures, a general methodology for the solid phase synthesis of these derivatives is also provided. Arrays of thiazolidinones, metathiazanones, and derivatives thereof useful as peptidomimetics and for the identification of agents having antifungal, antihistaminic, or antimicrobial activity or use in the treatment of inflammation, hypertension, renal failure, congestive heart failure, uremia and other conditions can be prepared using this method.

11 Claims, 18 Drawing Sheets

Stepwise vs. One-Pot Condensations
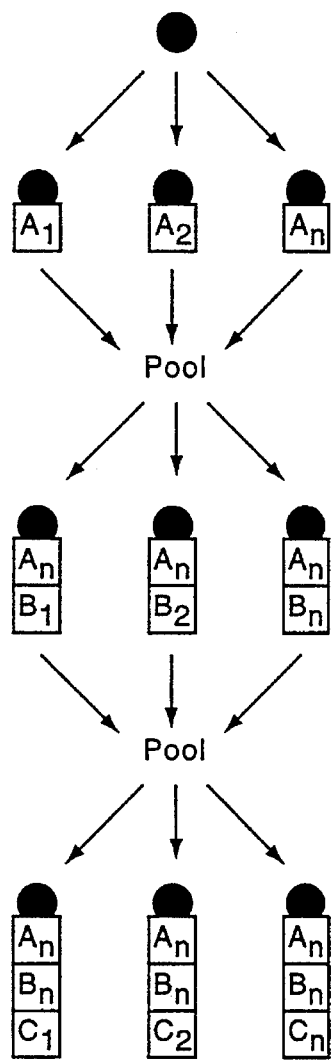
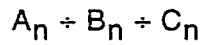
n = 3, then 9 reactions
n = 10, then 30 reactions
n = 36, then 108 reactions
Figure 5a
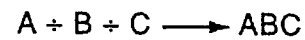
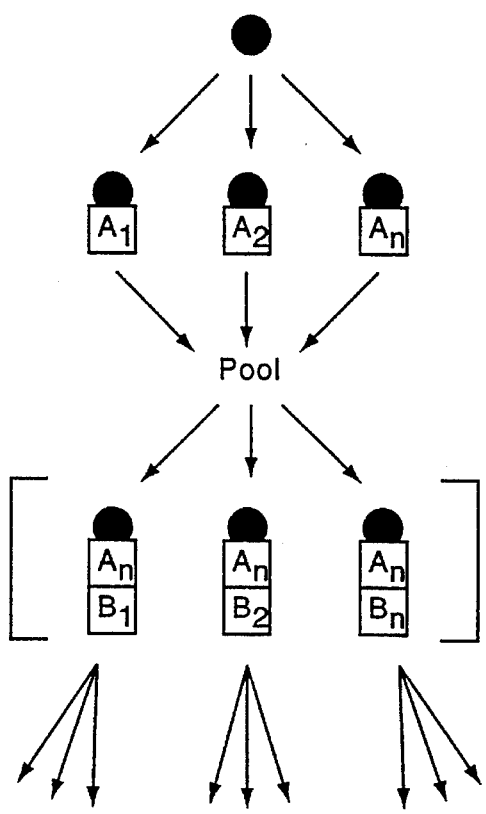
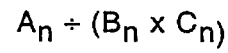
n = 3, then 12 reactions
n = 10, then 110 reactions
n = 36, then 1332 reactions
Figure 5b
Figure 5a & 5b Figure 6a
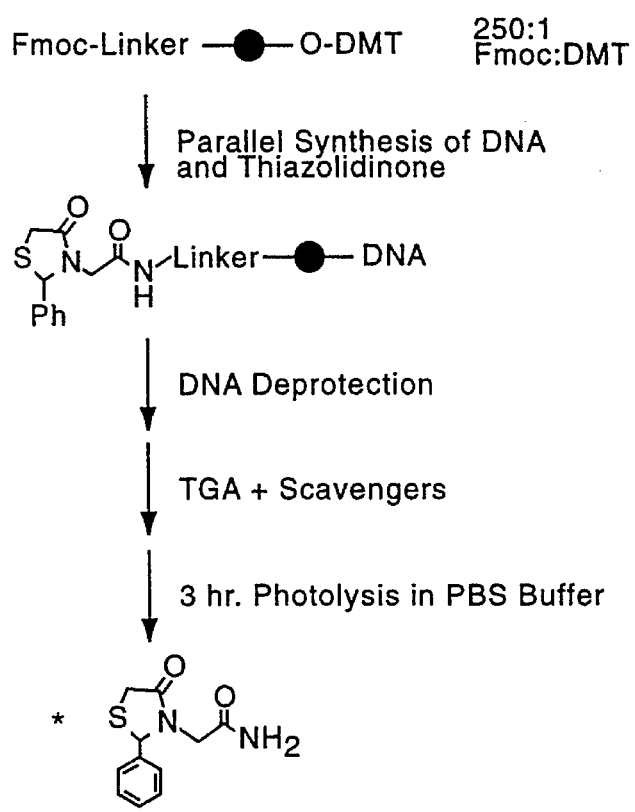
Figure 6b
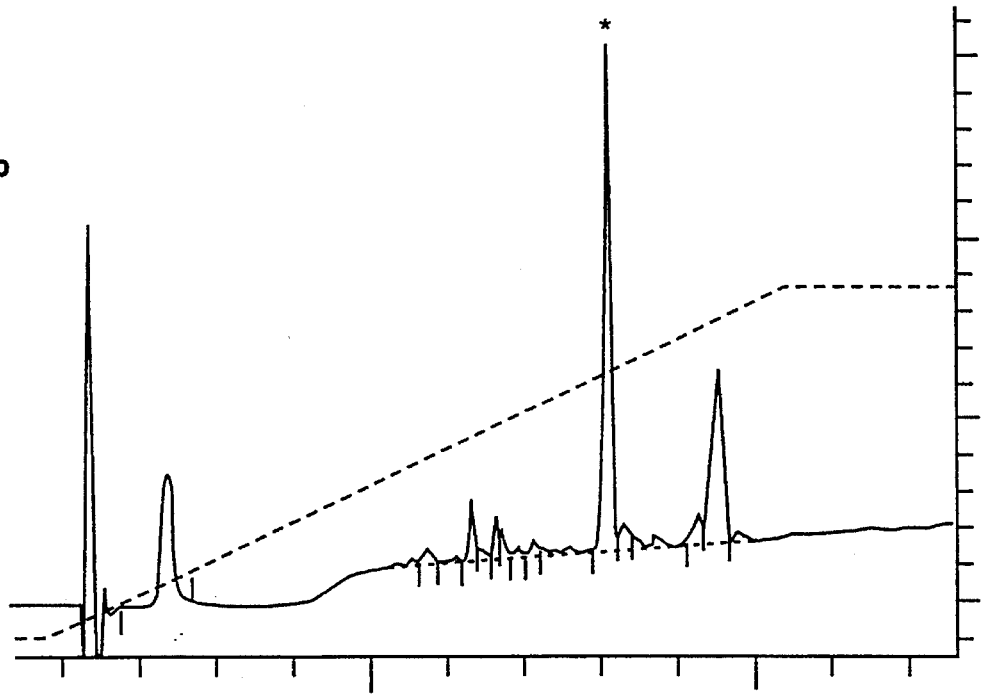
Figure 6a & 6b Potential Mimetic Structures
Mimetic                          Components
Figure 7a
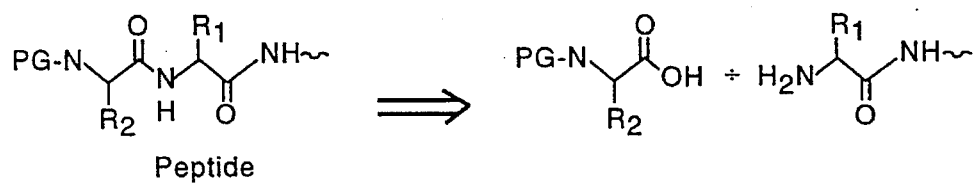
Peptide
Figure 7b
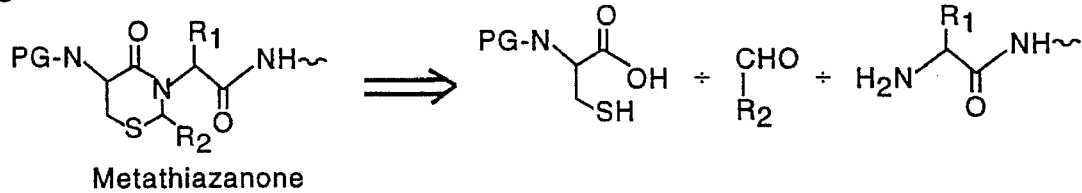
Metathiazanone
Figure 7c
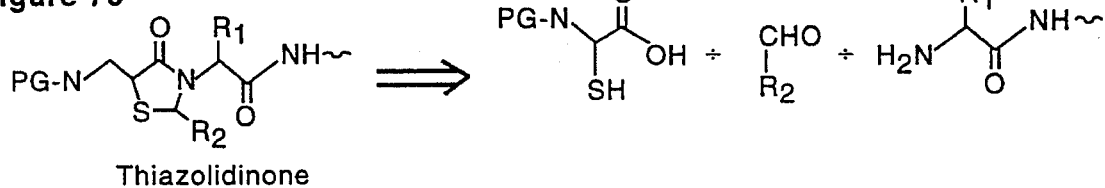
Thiazolidinone
Figure 7d
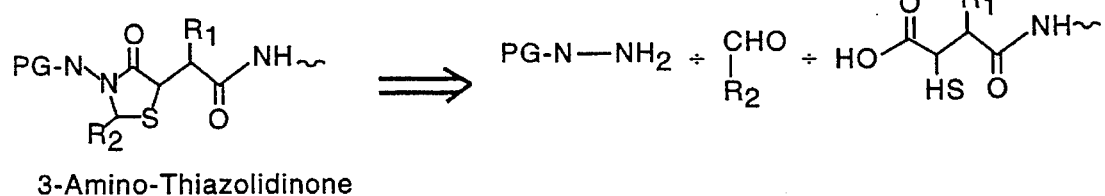
3-Amino-Thiazolidinone
Figure 7a - 7d

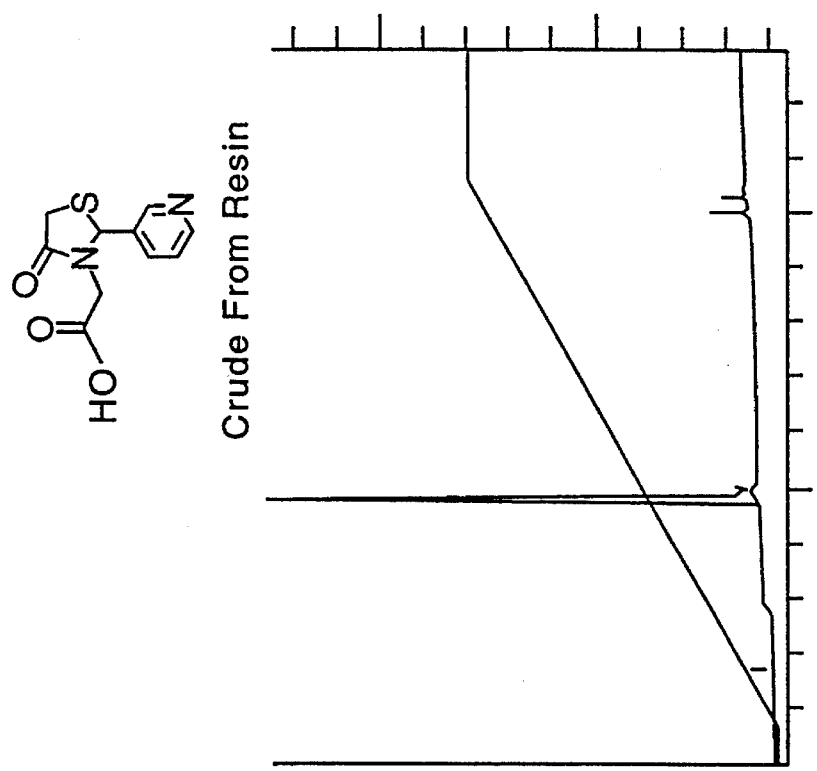
Figure 8b
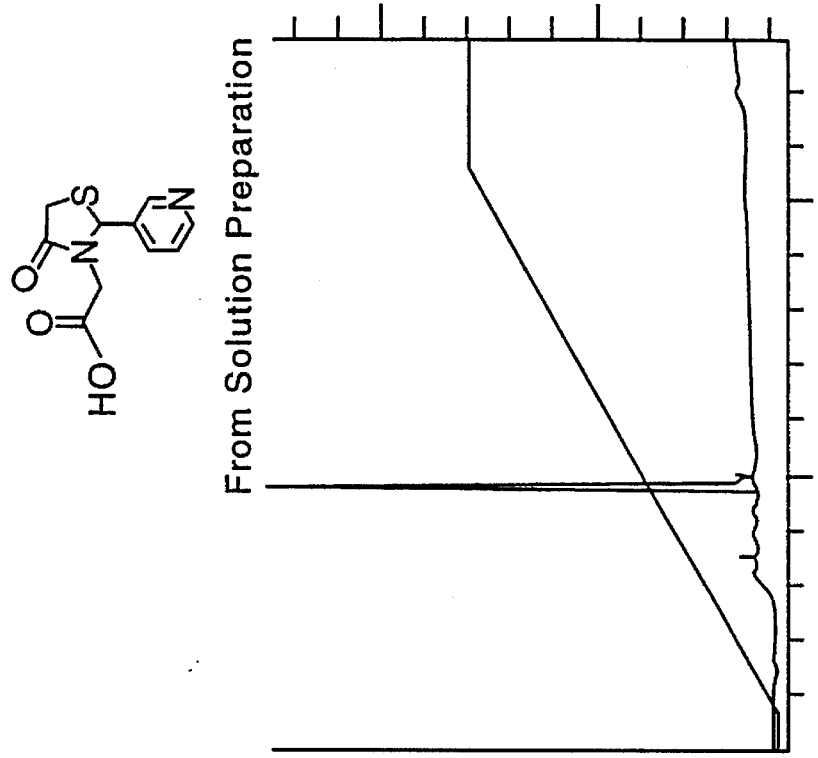
Figure 8a
Figure 8a & 8b

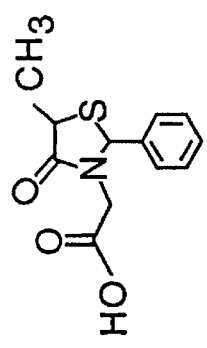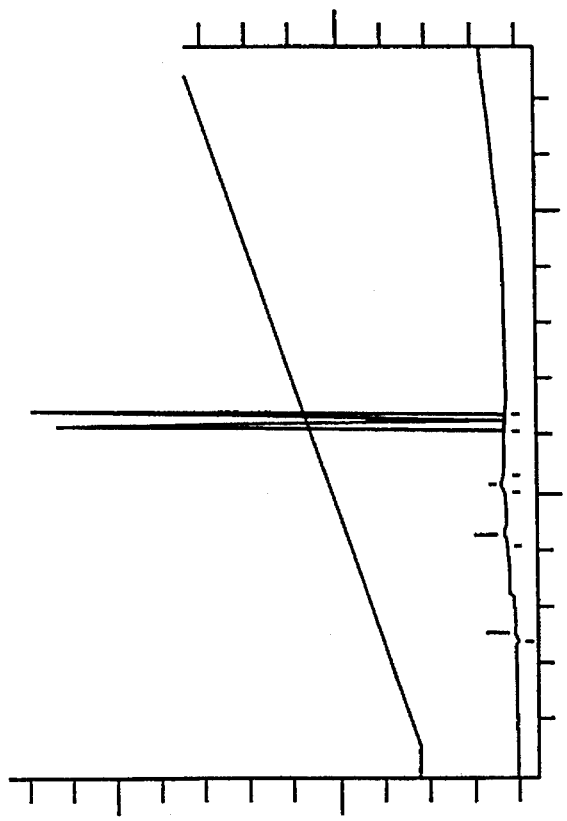
Figure 9b
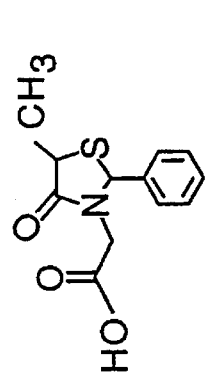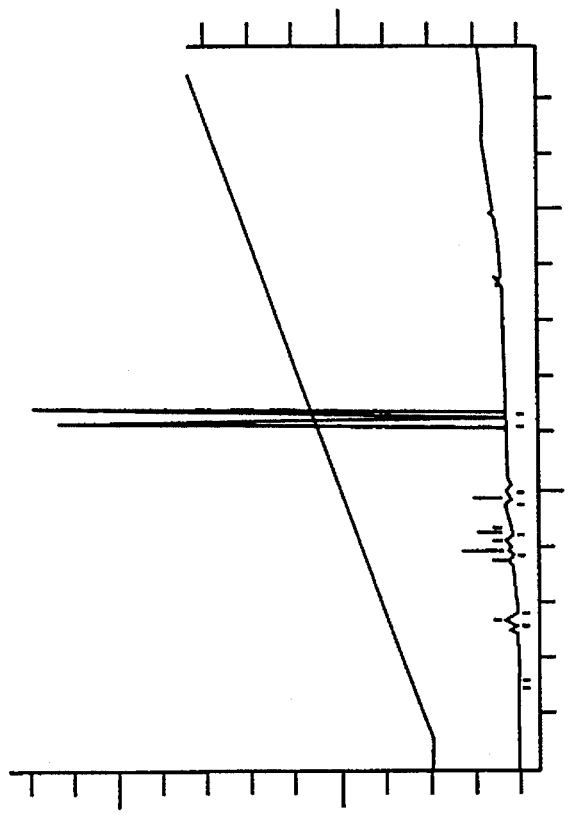
Figure 9a
Figure 9a & 9b

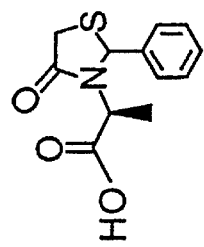
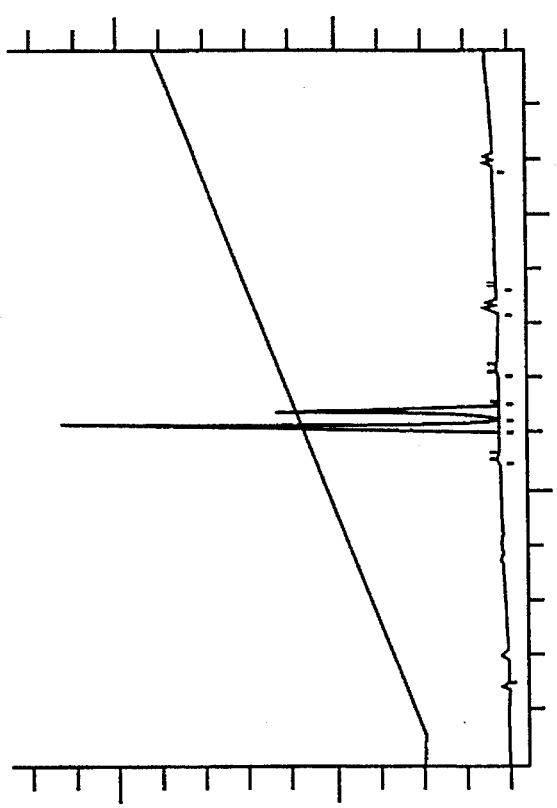
Figure 10b
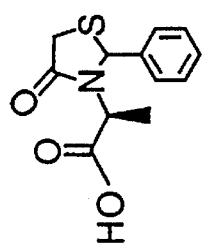
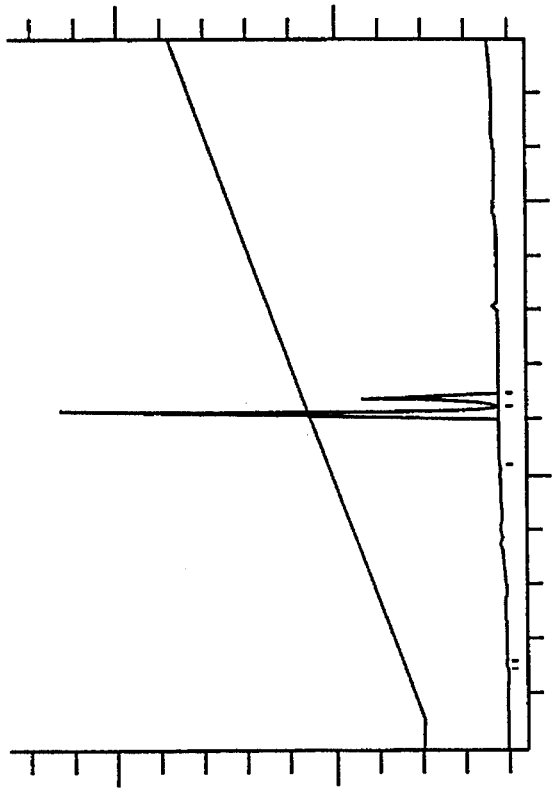
Figure 10a
Figure 10a & 10b

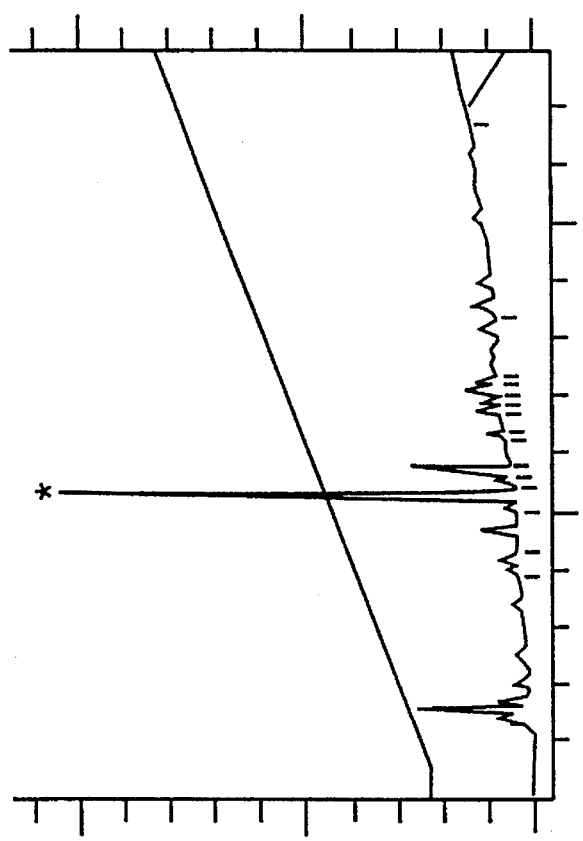
Figure 11a
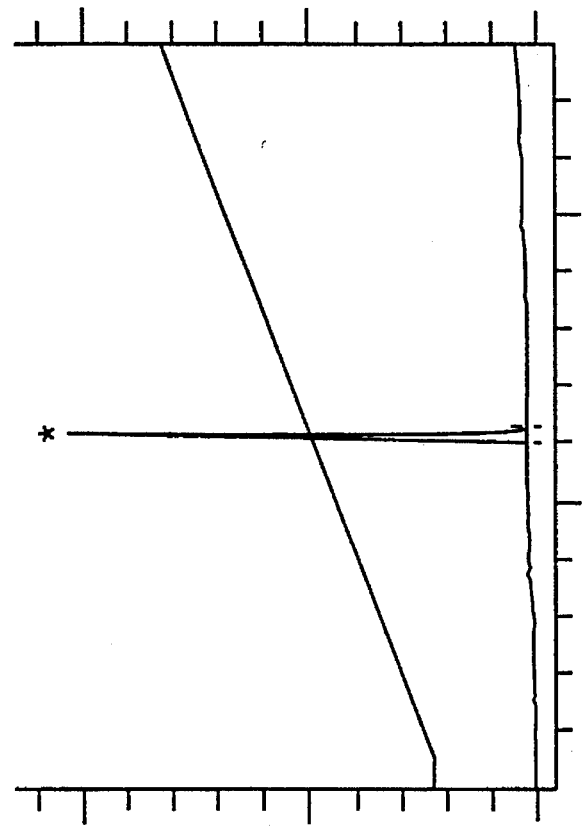
Figure 11b
Figure 11a & 11b

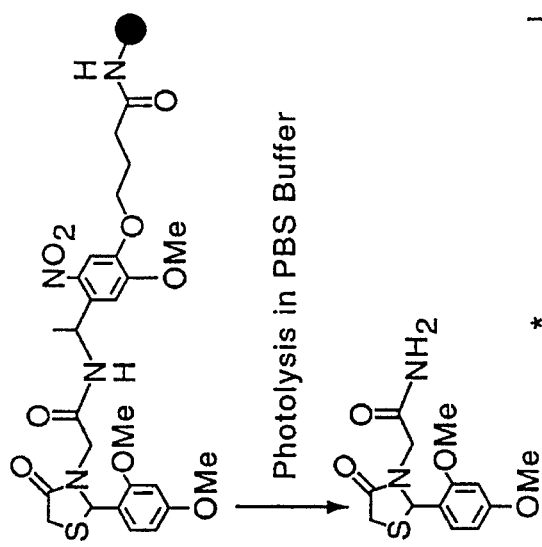
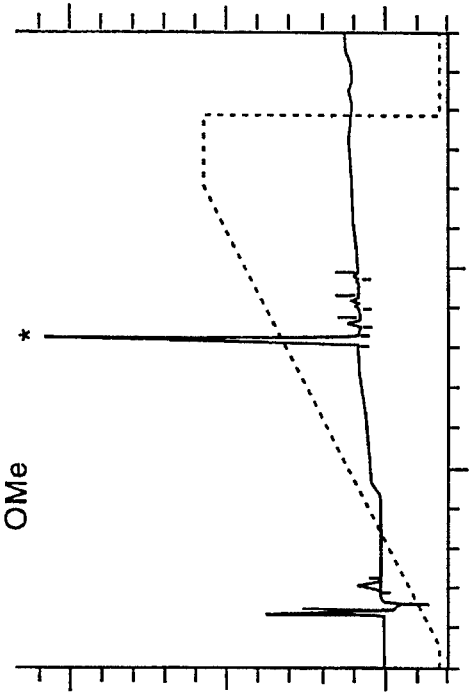
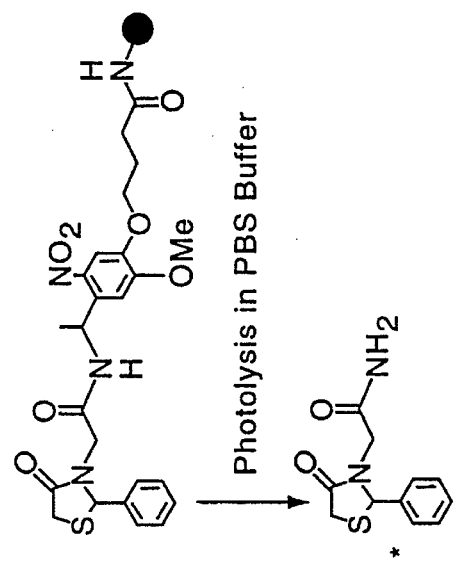
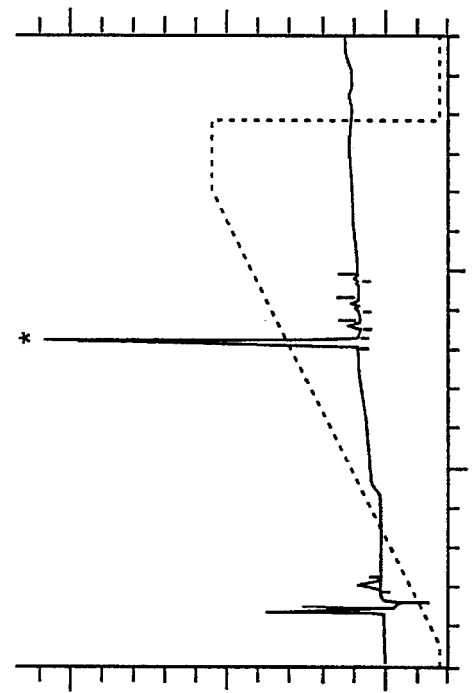
Figure 15a & 15b
Figure 15b
Figure 15a

METHODS FOR THE SOLID PHASE SYNTHESIS OF THIAZOLIDINONES, METATHIAZANONES, AND DERIVATIVES THEREOF

BACKGROUND OF THE INVENTION

The present invention is related to the area of chemical synthesis. More specifically, one embodiment of the present invention provides methods for the solid phase and combinatorial synthesis of 4-thiazolidinones, metathiazanones and derivatives thereof.

Obtaining a better understanding of the important factors in molecular recognition in conjunction with developing potent new therapeutic agents is a major focus of scientific research. Chemical and biological methods have recently been developed for the generation of large combinatorial libraries of peptides and oligonucleotides that are then screened against a specific receptor or enzyme in order to determine the key molecular recognition elements of the biopolymer for that receptor or enzyme. See U.S. Pat. No. 5,143,854; Ser. No. 07/805,727, filed Dec. 6, 1991, now U.S. Pat. No. 5,424,186; Ser. No. 07/624,120, filed Dec. 6, 1990, now abandoned; Ser. No. 07/946,239, filed Sep. 16, 1992, still pending; Ser. No. 07/762,522, filed Sep. 18, 1991, now abandoned; Ser. No. 07/978,940, filed Nov. 19, 1992, now abandoned; and Ser. No. 07/971,181, filed Nov. 2, 1992, now abandoned; each of which is assigned to the assignee of the present invention and incorporated herein by reference for all purposes. These methods provide rapid and efficient means to synthesize polymers that are biocompatible, i.e., compounds that are non-toxic and readily absorbed, and ideally are synthesized from monomers available in large quantity, with a reasonable shelf life, optical activity, high-fidelity coupling chemistry, and stable to various chemical reagents used for protecting and deprotecting various side chains.

Virtually any bioavailable organic compound can be accessed by chemical synthesis; however, such compounds typically are still synthesized and evaluated one at a time in many cases, thus dramatically limiting the number of derivatives which can be studied. This limitation can be overcome by developing the methodology for the combinatorial synthesis of large numbers of derivatives of therapeutically important classes of bioavailable organic compounds. Screening these compounds against key receptors or enzymes would then greatly accelerate the acquisition of useful structure versus recognition data and would revolutionize the search for potent new therapeutic agents.

The search for suitable small organic molecules amenable to a combinatorial synthesis approach is an ongoing quest. One ideal goal is to tailor the chemistry used to assemble the molecules to work in a polymer-supported fashion, in analogy to solid phase techniques commonly employed for peptides and oligonucleotides. The advantages of such a goal is twofold: not only does one gain overall efficiency through the ability to filter away both byproducts and excess reagents, but one also raises the possibility of mass screening of the immobilized molecules with techniques such as VLSIPS™ and ESL technologies. See, U.S. Pat. No. 5,143,854; Ser. No. 07/805,727, filed Dec. 6, 1991, U.S. Pat. No. 5,424,186; Ser. No. 07/624,120, filed Dec. 6, 1990, now abandoned; Ser. No. 07/946,239, filed Sep. 16, 1992, still pending; and Ser. No. 07/762,522, filed Sep. 18, 1991, now abandoned; each of which is assigned to the assignee of the present invention and incorporated herein by reference for all purposes.

Perhaps the first example of the application of combinatorial organic synthesis to non-polymeric organic compounds can be found in the work of Ellman who described the solid phase synthesis of a 1,4-benzodiazepines. See U.S. Pat. No. 5,288,514, which is incorporated herein by reference for all purposes. The benzodiazepines were synthesized on a solid support by the connection of three building blocks: an amino benzophenone; an amino acid; and an alkylating agent.

Hobbs Dewitt has reported on the generation of libraries of small molecules, which she terms "diversomers". Target compounds, including dipeptides, hydantoins, and benzodiazepenes, were synthesized simultaneously but separately, on a solid support in an array format, to generate a collection of up to 40 discrete structurally related compounds. The key step in this strategy involves the revealing of distal functionality which initiates attack on the bond linking the compound to the resin, thus, releasing the product from the resin.

In addition to the small organic molecules discussed above, another important class of molecules is the 4-thiazolidinones (herein referred to as thiazolidinones), metathiazanones, and derivatives thereof. The generic structure and numbering system of these compounds is shown below:

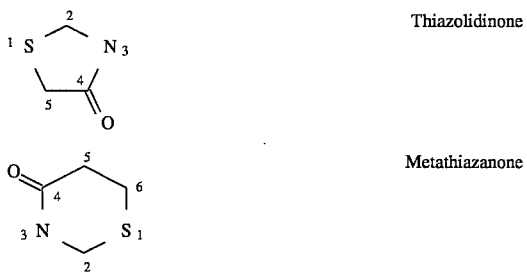

Thiazolidinone

Metathiazanone

Substituted 4-thiazolidinones possess many properties important for biological activity, such as optical activity and the ability to form hydrogen bonds and to carry side chain functionalities. Thiazolidinones have been shown to exhibit antifungal (see, e.g., Srivastava et al. (1991) *Ind. J. Chem.* 30:620–623; and Abdel-Rahman et al. (1990) *J. Ind. Chem. Soc.* 67:61–64); antihistaminic (see, e.g., Diurno et al. (1992) *J. Med. Chem.* 35:2910–1912); anti-platelet aggregation factor (see, e.g., Tanabe et al. (1991) *Tetrahedron Lett.* 32:379–382; and Tanabe et al. (1991) *Tetrahedron Lett.* 32:383–386); and antimicrobial (see, e.g., Hogale et al. (1991) *Ind. J. Chem.* 306:717–720) activities. In addition, this class of compounds has found use in the treatment of inflammation, hypertension, renal failure, congestive heart failure, uremia and other conditions. See, e.g., Walsh and Uwaydah, U.S. Pat. Nos. 5,061,720 and 4,225,609. 4-Thiazolidinones are therefore prime candidates for drug studies.

4-Thiazolidinones have been synthesized via the condensation of an aldehyde, an amine and a mercaptoacetic acid to generate the five-membered ring with the concomitant loss of two molecules of water. See, e.g., Diurno et al. (1992) *J. Med. Chem.* 35:2910–1912; Surrey and Cutler (1954) *J. Am. Chem. Soc.* 76: 578–580; and El-Kohry (1992) *OPPI Briefs* 24:81–83. The most likely mechanism for this condensation involves initial imine formation between the aldehyde and the amine, followed by addition of the thiol to the carbon-nitrogen double bond and finally ring closure. Treatment of an imine with a mercaptoacetic acid also generates a thiazolidinone in high yield. See Srivastava et al. supra;

Abdel-Rahman et al. supra; and Tanabe et al. supra. The synthesis of metathiazanones proceeds through the analogous reaction of an amine, aldehyde, and β-mercaptopropionic acid.

Unfortunately, there has been a lack of efficient techniques for synthesizing immobilized 4-thiazolidinones and particularly, for producing arrays of 4-thiazolidinones. The present invention meets this need.

SUMMARY OF THE INVENTION

The invention provides a rapid approach for combinatorial synthesis and screening of libraries of 4-thiazolidinones, metathiazonones, and derivatives thereof which overcomes the above-described limitations of current methodologies.

In one aspect, the present invention provides a method for the solid phase synthesis of thiazolidinones, metathiazonones, and derivatives thereof, which method includes the steps of first coupling an amine component to a solid support and then treating the immobilized amine component with a carbonyl component and a thiol component. In another aspect, the present invention provides a method for the solid state synthesis of thiazolidinones, metathiazonone, and derivatives thereof, which method includes the steps of first coupling a thiol component to a solid support and treating the immobilized thiol component with an amine component and a carbonyl component.

According to either embodiment, the amine component preferably comprises a primary amino group having the formula: $R-NH_2$, wherein R is selected from the group consisting of alkyl, alkoxy, amino, aryl, aryloxy, heteroaryl, and arylalkyl or salts thereof. According to the latter embodiment, R can also be hydrogen. More preferably, the amine component will have the formula:

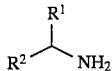

wherein $R^1$ and $R^2$ are independently selected from the groups consisting of hydrogen, alkyl, alkoxy, aryl, aryloxy, heteroaryl, carboxyl, carboxyalkyl, and arylalkyl. More preferably, the amine component will comprise an amino acid or peptide. Alternatively, according to either embodiment, the amine component may comprise a hydrazine derivative having the formula $R^1NHNH_2$ where $R^1$ is as described above, or a hydrazide derivative having the formula $R^1(CO)NHNH_2$ where $R^1$ is as described above. In addition, if the thiol component is immobilized, a monoprotected hydrazine having the formula $PGNHNH_2$ wherein PG is an acid-labile, base-labile, or photocleavable protecting group can serve as the amine component.

The carbonyl component preferably has the formula:

wherein $R^3$ and $R^4$ are independently selected from-the groups consisting of hydrogen, alkyl, aryl, heteroaryl, carboxyl, carboxyalkyl, and arylalkyl, provided that both $R^3$ and $R^4$ are not hydrogen. More preferably, the carbonyl component comprises an aldehyde and thus, either $R^3$ or $R^4$ is hydrogen. In a still more preferred embodiment, either $R^3$ or $R^4$ is hydrogen with the other being selected from the group consisting an aromatic group or a heteroaromatic group.

The thiol component preferably comprises a mercapto carboxylic acid having the formula:

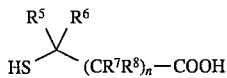

wherein $R^5$, $R^6$, $R^7$, and $R^8$ are independently selected from the groups consisting of hydrogen, alkyl, alkoxy, aryl, aryloxy, heteroaryl, carboxyl, carboxyalkyl, and arylalkyl and n is either 0 or 1 wherein n being 0 represents a valence bond.

According to either embodiment, the addition of the various components to the immobilized component can be sequential with, for example, the carbonyl component being added first to the immobilized amine component to form an immobilized imine and then adding the thiol component to complete the condensation reaction, or simultaneous with all of the components being combined in a one-step reaction. In addition, the condensation reaction can be performed once to yield a support-bound thiazolidinone, metathiazanone, or derivative thereof or repeatedly to yield a support-bound polymer having at least two thiazolidinones, metathiazanones, and/or derivatives.

In a particularly preferred embodiment, a mixture of primary amines, aldehydes, and/or a mixture of α-mercapto carboxylic acids and/or a mixture of β-mercapto carboxylic acids are used to produce a library or array of solid support-bound thiazolidinones, metathiazanones, or derivatives thereof. These libraries will find use in the identification of specific thiazolidinones, metathiazonones, and derivatives thereof having antifungal, antihistaminic, or antimicrobial activity or use in the treatment of inflammation, hypertension, renal failure, congestive heart failure, uremia and other conditions.

BRIEF DESCRIPTION OF THE DRAWINGS

FIG. 5 illustrates a comparison between the number of reactions required in a stepwise and in a one-pot condensation reaction with three components.

FIG. 6 shows a HPLC trace for the products obtain from the parallel synthesis of a thiazolidinone prepared from benzaldehyde, glycine, and mercaptoacetic acid with an oligonucleotide tag after cleavage from the resin.

FIG. 7 illustrates how thiazolidinones, 3-amino-thiazolidinones, and metathiazanones can serve as peptidomimetics and methods for their preparation.

FIG. 8 shows HPLC traces for the products of a solution preparation and a solid state synthesis of a thiazolidinone prepared from glycine, mercaptoacetic acid, and 3-pyridinecarboxaldehyde.

FIG. 9 shows HPLC traces for the products of a solution preparation and a solid state synthesis of a thiazolidinone prepared from glycine, thiolactic acid, and benzaldehyde.

FIG. 10 shows HPLC traces for the products of a solution preparation and a solid state synthesis of a thiazolidinone prepared from alanine, mercaptoacetic acid, and benzaldehyde.

FIG. 11 shows HPLC traces for the products of a solution preparation and a solid state synthesis of a metathiazanone prepared from glycine, β-mercaptopropionic acid, and benzaldehyde.

FIG. 15 shows HPLC traces for the products from photolysis in PBS buffer for two thiazolidinones.

DESCRIPTION OF THE PREFERRED EMBODIMENT

Figures 1A, 1B, 1C, 1D:
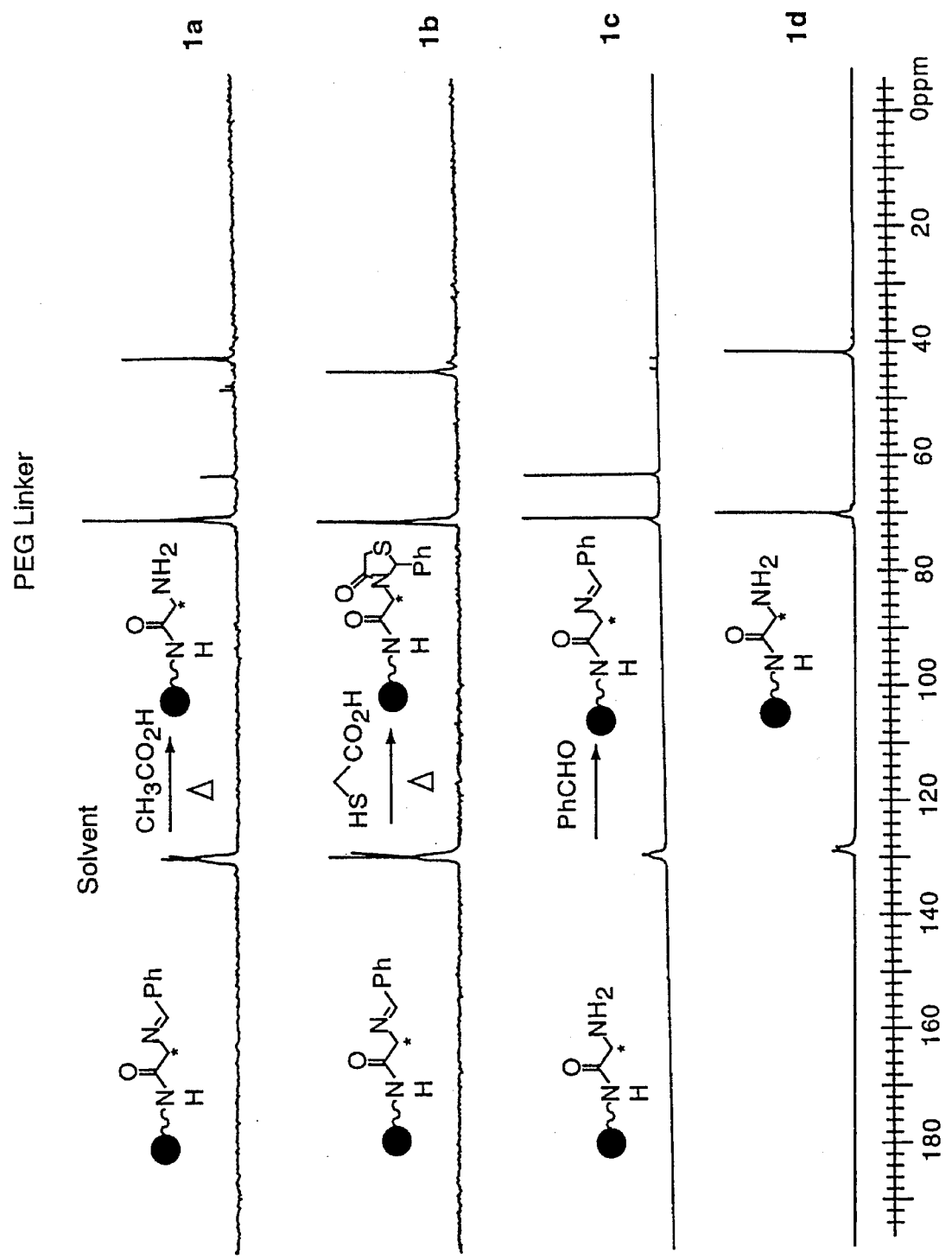
FIG. 1 illustrates the use of $^{13}C$ NMR to monitor the condensation reaction of support-bound glycine with benzaldehyde and mercaptoacetic acid. Panel D shows the $^{13}C$ NMR spectrum of support-bound glycine which has been labeled with a $^{13}C$-atom at the position alpha to the carbonyl. Panel C shows the $^{13}C$ NMR spectrum of the support-bound labeled imine produced by the reaction of support-bound labeled glycine with benzaldehyde. Panel B shows the $^{13}C$ NMR spectrum of the labeled thiazolidinone produced by the reaction of support-bound labeled imine with mercaptoacetic acid. Panel A shows the $^{13}C$ NMR spectrum of the product of the reaction of support-bound labeled imine with acetic acid.

The description of the invention is provided as indicated by the following outline. In addition, Section I provides for a glossary of terms to facilitate the description of the invention. A number of terms and abbreviations are defined to have the general meanings indiated as used herein to describe the invention.

OUTLINE

I. Terminology
II. Description of the Invention
  A. Overview
  B. The Solid Support
    1. Nature of the Support
    2. Linkers
    3. Immobilization
  C. The Amine Component
  D. The Carbonyl Component
  E. The Thiol Component
  F. The Exogenous Base
  G. The Reaction Conditions
    1. Immobilization
    2. Reaction Temperature
    3. Solvent
    4. Dehydrating Agent
    5. Stereochemistry
    6. Polymer Preparation
  H. Preparation of Derivatives of Thiazolidinones and Metathiazonones
  I. Cleavage
  J. Analysis of the Thiazolidinones
III. Preparation of Arrays of Thiazolidinones
  A. General Overview
  B. Preparation of Encoded Libraries
    1. Overview
    2. The Identifier Tag
  C. Preparation of Arrays using the VLSIPS™ technique
  D. Other Methods E. Instrumentation
IV. Utility
  A. Thiazolidinones and Derivatives As Peptidomimetics
  B. Thiazolidinones and Derivatives As Therapeutics
V. Assays I. Terminology Unless otherwise stated, the following terms used in the specification and claims have the meanings given below:

"Alkoxy" refers to the group alkyl-O-.

"Alkyl" refers to a cyclic, branched, or straight chain chemical group containing only carbon and hydrogen, such as methyl, heptyl, —$(CH_2)_2$—, and adamantyl. Alkyl groups can either be unsubstituted or substituted with one or more substituents, e.g., halogen, alkoxy, acyloxy, amino, aryl, hydroxyl, mercapto, carboxy, benzyloxy, phenyl, benzyl, or other functionality which may be suitably blocked, if necessary for purposes of the invention, with a protecting group. Typically, alkyl groups will comprise 1 to 12 carbon atoms, preferably 1 to 10, and more preferably 1 to 8 carbon atoms.

"Amino" or "amine group" refers to the group —NR'R", where R' and R" are independently selected from the group consisting of hydrogen, alkyl, substituted alkyl, aryl, substituted aryl, aryl alkyl, substituted aryl alkyl, heteroaryl, and substituted heteroaryl. In a primary amino group, both R' and R" are hydrogen, whereas in a secondary amino group, either, but not both, R' or R" is hydrogen.

An "α-amino acid" consists of a carbon atom, called the α-carbon, to which is bonded an amino group and a carboxyl group. Typically, this α-carbon atom is also bonded to a hydrogen atom and a distinctive group referred to as a "side chain." The hydrogen atom may also be replaced with a group such as alkyl, substituted alkyl, aryl, substituted aryl, heteroaryl, and other groups. The side chains of naturally occurring amino acids are well known in the art and include, for example, hydrogen (as in glycine), alkyl (as in alanine (methyl), valine (isopropyl), leucine (sec-butyl), isoleucine (iso-butyl), and proline (—$(CH_2)_3$—)), substituted alkyl (as in serine (hydroxymethyl), cysteine (thiomethyl), aspartic acid (carboxymethyl), asparagine, arginine, glutamine, glutamic acid, and lysine), aryl alkyl (as in phenylalanine, histidine, and tryptophan), substituted aryl alkyl (as in tyrosine and thyroxine), and heteroaryl (as in histidine). See, e.g., Harper et al. (1977) *Review of Physiological Chemistry*, 16th Ed., Lange Medical Publications, pp. 21–24.

In addition to naturally occurring side chains, the amino acids used in the present invention may possess synthetic side chains. A "synthetic side chain" is any side chain not found in a naturally occurring amino acid. For example, a synthetic side chain can be an isostere of the side chain of a naturally occurring amino acid. Naturally occurring and synthetic side chains may contain reactive functionalities, such as hydroxyl, mercapto, and carboxy groups. One skilled in the art will appreciate that these groups may have to be protected to carry out the desired reaction scheme. As stated above, the hydrogen at the α-carbon can also be replaced with other groups; those of skill in the art recognize the medicinal importance of α-methyl amino acids and other α-, α-disubstituted amino acids.

"Aryl" or "Ar" refers to an aromatic carbocyclic group having a single ring (e.g., phenyl) or multiple condensed rings (e.g., naphthyl or anthryl), which can optionally be unsubstituted or substituted with amino, hydroxyl, lower alkyl, alkoxy, aryloxy, chloro, halo, mercapto, and other substituents. Preferred aryl groups include phenyl, 1-naphthyl, 2-naphthyl, biphenyl, phenylcarboxylphenyl (i.e., derived from benzophenone), and the like.

"Aryloxy" refers to the group aryl-O- or heteroaryl-O-.

"Arylalkyl" refers to the groups R'—Ar and R-HetAr, where Ar is an aryl group, HetAr is a heteroaryl group, and R' is straight-chain or branched-chain aliphatic group. Examples of arylalkyl groups include benzyl and furfuryl.

"Carboxy" or "carboxyl" refers to the group —R'(COOH) where R' is alkyl, substituted alkyl, aryl, substituted aryl, aryl alkyl, substituted aryl alkyl, heterocyclic, heteroaryl, or substituted heteroaryl.

"Carboxyalkyl" refers to the group —(CO)—R' where R' is alkyl or substituted alkyl.

"Carboxyaryl" refers to the group —(CO)—R' where R' is aryl, heteroaryl, or substutited aryl or heteroaryl.

"Chemical library" or "array" is an intentionally created collection of differing molecules which can be prepared either synthetically or biosynthetically and screened for biological activity in a variety of different formats (e.g., libraries of soluble molecules; and libraries of compounds tethered to resin beads, silica chips, or other solid supports). The term is also intended to refer to an intentionally created collection of stereoisomers.

"Combinatorial synthesis strategy" or "combinatorial chemistry" refers to an ordered strategy for the parallel synthesis of diverse compounds by sequential addition of reagents which leads to the generation of large chemical libraries. Thus, combinatorial chemistry refers to the systematic and repetitive, covalent connection of a set of different "building blocks" of varying structures to each other to yield large arrays of diverse molecular entities.

"Exogenous base" refers to nonnucleophilic bases such as alkali metal acetates, alkali metal carbonates, alkaline metal carbonates, alkali metal bicarbonates, tri(lower alkyl) amines, and the like, for example, sodium acetate, potassium bicarbonate, calcium carbonate, diisopropylethylamine, triethylamine, and the like.

"Heteroaryl" or "HetAr" refers to a monovalent unsaturated aromatic carbocyclic group having a single ring (e.g., pyridyl or furyl) or multiple condensed rings (e.g., indolizinyl or benzothienyl) and having at least one hetero atom, such as N, O, or S, within the ring, which can optionally be unsubstituted or substituted with amino, hydroxyl, alkyl, alkoxy, halo, mercapto, and other substituents.

"Identifier tag" denotes a physical attribute that provides a means whereby one can identify a chemical reaction. The identifier tag serves to record a step in a series of reactions used in the synthesis of a chemical library. The identifier tag may have any recognizable feature, including for example: a microscopically or otherwise distinguishable shape, size, mass, color, optical density, etc.; a differential absorbance or emission of light; chemical reactivity; magnetic or electronic properties; or any other distinctive mark capable of encoding the required information, and decipherable at the level of one (or a few) molecules. A preferred example of such an identifier tag is an oligonucleotide, because the nucleotide sequence of an oligonucleotide is a robust form of encoded information. Identifier tags can be coupled to the solid support. Alternatively, the "identifier tag" can be coupled directly to the compound being synthesized, whether or not a solid support is used in the synthesis. In the latter embodiment, the identifier tag can conceptually be viewed as also serving as the "support" for synthesis.

"Limiting reagent" refers to that substance which limits the maximum amount of product formed in a chemical reaction, no matter how much of the other reactants remains.

"Linker" refers to a molecule or group of molecules attached to a solid support and spacing a synthesized compound from the solid support, such as for exposure/binding to a receptor.

"Predefined region" refers to a localized area on a solid support which is, was, or is intended to be used for formation of a selected molecule and is otherwise referred to herein in the alternative as a "selected" region. The predefined region may have any convenient shape, e.g., circular, rectangular, elliptical, wedge-shaped, etc. For the sake of brevity herein, "predefined regions" are sometimes referred to simply as "regions." In some embodiments, a predefined region and, therefore, the area upon which each distinct compound is synthesized is smaller than about 1 cm$^2$ or less than 1 mm$^2$. Within these regions, the molecule synthesized therein is preferably synthesized in a substantially pure form. In additional embodiments, a predefined region can be achieved by physically separating the regions (i.e., beads, resins, gels, etc.) into wells, trays, etc.

"Protecting group" refers to a chemical group that exhibits the following characteristics: (1) reacts selectively with the desired functionality in good yield to give a derivative that is stable to the projected reactions for which protection is desired; 2) can be selectively removed from the derivatized solid support to yield the desired functionality; and 3) is removable in good yield by reagents compatible with the other functional group(s) generated in such projected reactions. Examples of protecting groups can be found in Greene et al. (1991) *Protective Groups in Organic Synthesis*, 2nd Ed. (John Wiley & Sons, Inc., New York). Preferred protecting groups include photolabile protecting groups (such as methylnitropiperonyloxycarbonyl (Menpoc), methylnitropiperonyl (Menp), nitroveratryl (Nv), nitroveratryloxycarbonyl (Nvoc), or nitroveratryloxymethyl ether (Nvom)); acid-labile protecting group (such as Boc or DMT); base-labile protecting groups (such as Fmoc, Fm, phosphonioethoxycarbonyl (Peoc, see Kunz (1976) *Chem. Ber.* 109:2670); groups which may be removed under neutral conditions (e.g., metal ion-assisted hydrolysis), such as DBMB (see Chattopadhyaya et al. (1979) *J.C.S. Chem. Comm.* 987–990), allyl or alloc (see, e.g., Greene and Wuts, "Protective Groups in Organic Synthesis", 2nd Ed., John Wiley & Sons, Inc., New York, N.Y. (1991), 2-haloethyl (see Kunz and Buchholz (1981) *Angew. Chem. Int. Ed. Engl.* 20:894), and groups which may be removed using fluoride ion, such as 2-(trimethylsilyl)ethoxymethyl (SEM), 2-(trimethylsilyl)ethyloxycarbonyl (Teoc) or 2-(trimethylsilyl)ethyl (Te) (see, e.g., Lipshutz et al. (1980) *Tetrahedron Lett.* 21:3343–3346)); and groups which may be removed under mild reducing conditions (e.g., with sodium borohydride or hydrazine), such as Lev. Id. at 30–31, 97, and 112. Particularly preferred protecting groups include Fmoc, Fm, Menpoc, Nvoc, Nv, Boc, CBZ, allyl, alloc, Npeoc (4-nitrophenethyloxycarbonyl) and Npeom (4-nitrophenethyloxymethyloxy).

"Solid support" or "support" refers to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. The solid support is alternatively referred to herein as a support.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation. The compounds of the instant invention may have one or more asymmetrical carbon atoms and therefore include various stereoisomers. All stereoisomers are included within the scope of the invention and within the scope of the term "thiazolidinone", "metathiazanone", or "derivative thereof".

Isolation and purification of the compounds and intermediates described herein can be effected, if desired, by any suitable separation or purification procedure such as, for example, filtration, extraction, crystallization, column chromatography, thin-layer chromatography, thick-layer (preparative) chromatography, distillation, or a combination of these procedures. Specific illustrations of suitable separation and isolation procedures can be had by references to the examples hereinbelow. However, other equivalent separation or isolation procedures can, of course, also be used.

Abbreviations: The following abbreviations are intended to have the following meanings:

Boc=t-butyloxycarbonyl

BOP=benzotriazol-1-yloxytris(dimethylamino) phosphonium hexafluorophosphate

DCC=dicyclohexylcarbodiimide

Ddz=dimethoxydimethylbenzyloxy

DIC=diisopropylcarbodiimide

DMT=dimethoxytrityl

Fmoc=fluorenylmethyloxycarbonyl

HBTU=2-(1H-benzotriazol-1-yl)-1,1,3,3-tetramethyluronium hexafluorophosphate

HOBt=1-hydroxybenzotriazole

Menpoc=methylnitropiperonyloxycarbonyl

Menp=methylnitropiperonyl

Nv=nitroveratryl

Nvoc=6-nitroveratryloxycarbonyl and other photoremovable groups

OPfp=pentafluorophenyloxy

OSu=N-succinimidyloxy (also known as NHS)

PG=protective group

TFA=trifluoroacetic acid

II. Description of the Invention

A. Overview

The present invention, in one aspect, includes a highly efficient and versatile method of synthesizing and screening, preferably in parallel and simultaneous fashion, large numbers of 4-thiazolidinones, metathiazanones and derivatives thereof. Thus, according to one aspect, the present invention provides a solid-phase synthesis method for 4-thiazolidinones, metathiazanones, and derivatives thereof in which variable substituent groups are attached to a common central structure. This solid-phase synthesis permits each reaction to be confined to a predefined region of a small solid structure. The physical joining of a multitude of small solid structures into a single unit, for example, then permits the simultaneous handling of a multitude of compounds and reagents. The use of structures of this kind for certain multiple simultaneous reactions is known in the art, and its application to the present invention will become apparent from the description which follows.

In order to expediently synthesize a combinatorial library of 4-thiazolidinones, metathiazanones, and derivatives thereof, a generalized methodology for the solid phase synthesis of these compounds is also provided. Synthesis on solid support proceeds in sufficiently high yield in preferred embodiments such that purification and isolation steps can be eliminated and thus, dramatically increasing synthesis efficiency. According to one embodiment, the method of synthesizing 4-thiazolidinones, metathiazanones, and derivatives thereof comprises the steps of first binding an amine component to a solid support. Preferably, the amine component will comprise a primary amine, and more preferably, an amino acid, a peptide, a mono-substituted hydrazine derivative or a hydrazide derivative. The heterocycle is then formed by treating the solid support-bound amine component, either sequentially or simultaneously, with a carbonyl component, preferably an aldehyde, and a thiol component, preferably an α—mercapto carboxylic acid or a β-mercapto carboxylic acid. According to another embodiment, the thiol component is immobilized on the support and the heterocycle is formed by treatment of the immobilized component with a carbonyl component, preferably an aldehyde, and an amine component, preferably an α-amino acid, a peptide, a monoprotected or mono-substituted hydrazine derivative or a hydrazide derivative.

B. The Solid Support

1. Nature of the Support

Typically, the libraries or arrays of the invention are composed of a collection of "solid supports". Such solid supports may be of any shape, although they preferably will be roughly spherical. The supports need not necessarily be homogenous in size, shape or composition; although the supports usually and preferably will be uniform. In some embodiments, supports that are very uniform in size may be particularly preferred. In another embodiment, two or more distinctly different populations of solid supports may be used for certain purposes.

"Solid support" embraces a particle with appropriate sites for oligomer synthesis and, in some embodiments, tag attachment and/or synthesis. Solid supports may consist of many materials, limited primarily by capacity for derivatization to attach any of a number of chemically reactive groups and compatibility with the synthetic chemistry used to produce the array and, in some embodiments the methods used for tag attachment and/or synthesis. Suitable support materials typically will be the type of material commonly used in peptide and polymer synthesis and include glass, latex, heavily cross-linked polystyrene or similar polymers, gold or other colloidal metal particles, and other materials known to those skilled in the art. Except as otherwise noted, the chemically reactive groups with which such solid supports may be derivatized are those commonly used for solid phase synthesis of the polymer and thus will be well known to those skilled in the art, i.e., carboxyls, amines and hydroxyls.

To improve washing efficiencies, one can employ nonporous supports or other solid supports less porous than typical peptide synthesis supports; however, for certain applications of the invention, quite porous beads, resins, or other supports work well and are often preferable. A preferred support is glass, as described in U.S. Pat. No. 5,143,854, supra. Another preferred solid support is resin, such as the beads described in co-pending U.S. patent application Ser. No. 07/946,239, filed Sep. 16, 1992, supra. In general, the bead size is in the range of 1 nm to 100 μm, but a more massive solid support of up to 1 mm in size may sometimes be used. Particularly preferred resins include Sasrin resin (a polystyrene resin available from Bachem Bioscience, Switzerland); and TentaGel S AC, TentaGel PHB, or TentaGel S NH$_2$ resin (polystyrene-polyethylene glycol copolymer resins available from Rappe Polymere, Tubingen, Germany). Other preferred supports are commercially available and described by Novabiochem, La Jolla, Calif.

2. Linkers

When bound to a solid support, the thiazolidinone and any associated tags are usually attached by means of one or more molecular linkers. The linker molecules preferably have lengths sufficient to allow the compounds to which they are bound to interact freely with any molecules exposed to the solid support surface, such as synthetic reagents or receptors which are an object of study. The linker molecule, prior to attachment, has an appropriate functional group at each end, one group appropriate for attachment to the support and the other group appropriate for attachment to the thiazolidinone or tag.

One can, of course, incorporate a wide variety of linkers, depending upon the application and the effect desired. For instance, one can select linkers that impart hydrophobicity, hydrophilicity, or steric bulk to achieve desired effects on properties such as coupling or binding efficiency. In one aspect of the invention, branched linkers, i.e., linkers with bulky side chains such as the linker, Fmoc-Thr(tBu), are used to provide rigidity to or to control spacing of the molecules on the solid support in a library or between a molecule and a tag in the library. In some embodiments, cleavable linkers will be used to facilitate an assay or detection step as discussed more fully below.

3. Immobilization

The choice of functionality used for binding a molecule to the solid support will depend on the nature of the compound to be synthesized and the type of solid support. Conditions for coupling monomers and polymers to solid supports through a wide variety of functional groups are known in the art. See, e.g., U.S. Pat. Nos. 4,542,102; 4,282,287; Merrifield, "Solid Phase Peptide Synthesis," *J. Am. Chem. Soc.*, (1963) 85:2149–2154; Geysen et al., "Strategies for Epitope Analysis Using Peptide Synthesis," *J. Imm. Meth.*, (1987) 102:259–274; Pirrung et at., U.S. Pat. No. 5,143,854; and Fodor et al., "Light-Directed Spatially-Addressable Parallel Chemical Synthesis," *Science* (1991) 251:767–773, each of which is incorporated herein by reference.

C. The Amine Component

According to the present invention, an amine component is coupled to a carbonyl component and a thiol component to yield a thiazolidinone or derivative thereof. The amine component can be utilized in a soluble format or can be attached to a solid support. According to the latter embodiment, the amine component will include a functionality which can covalently bind the molecule to the solid support (e.g., an activated carbonyl, acyl halide, or activated hydroxyl) as well as the amino group or a protected derivative thereof.

Typically the amine component will comprise a primary amine having the formula: R—NH$_2$, wherein R is selected from the group consisting of hydrogen (i.e., an amine salt as a further valence is necessary to attach the amine component to the solid support), alkyl, alkoxy, amino, aryl, aryloxy, heteroaryl, and arylalkyl or salts thereof. More preferably, the amine component will have the formula:

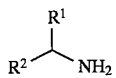

wherein $R^1$ and $R^2$ are independently selected from the groups consisting of hydrogen, alkyl, alkoxy, aryl, aryloxy, heteroaryl, carboxyl, carboxyalkyl, carboxyaryl, and arylalkyl. The amine component, if not commercially available, can be prepared by standard chemical procedures.

In a preferred embodiment, the amine component will comprise an amino acid, and more preferably, an amino acid bearing a substituent on the alpha carbon. The amino acids finding utility in the present invention include the twenty naturally occurring α-amino acids, in either their D- or L-enantiomeric forms. Unnatural amino acids such as α, α-disubstituted amino acids, N-alkyl amino acids, lactic acid, and other unconventional amino acids are also suitable components. Examples of unconventional amino acids include, but are not limited to: 4-hydroxyproline, O-phosphoserine, 3-methylhistidine, 5-hydroxylysine, and other similar amino acids. Since peptides are composed of amino acid subunits, one of skill in the art will appreciate that peptides can also serve as amine components.

Alternatively, the amine component may comprise a mono-protected hydrazine having the formula $PGNHNH_2$ wherein PG is an appropriate acid-labile (e.g., Boc), base-labile (Fmoc), or photocleavable protecting group; a mono-substituted hydrazine derivative having the formula $R^1NHNH_2$ where $R^1$ is alkyl, alkyoxy, aryl, aryloxy, heteroaryl, carboxyl, carboxyalkyl, carboxyaryl, and arylalkyl; or a hydrazide derivative having the formula $R^1(CO)NHNH_2$ where $R^1$ is as described above.

According to another aspect of this invention, the solid support will be derivatized such that the amine component comprises a surface amino group on the solid support. For example, thiazolidinones can be prepared from the primary amino group of the Knorr linker (a linker having a free benzhydryl or benzyl amine group) or other suitable cleavable linker or from the primary amino group found on the surface of TentaGel S $NH_2$ resin. When a primary amino group of a cleavable linker serves as the amine component, cleavage from the support affords the unsubstituted thiazolidinone or metathiazanone (i.e., where the nitrogen atom in the ring bears a hydrogen atom). Thus, the surface amino group can serve as an ammonia equivalent.

In other aspects of this invention, the amine component will comprise the primary amine of a carbamate or urea-type polymer. Procedures for the preparation of these types of materials can be found in U.S. patent application Ser. No. 08/147,805, filed Nov. 3, 1993; and Cho et al. (1993) Science 261:1303–1305, each of which is incorporated herein by reference.

If the amine component possesses reactive sites other than the amino group, it may be necessary to protect them during the synthesis. Suitable protecting groups include acid-labile, base-labile, photoremovable, or removable under neutral conditions. See, e.g., Green, *Protecting Groups in Organic Synthesis*, Wiley 1985, pp. 218–288, which is incorporated herein by reference. The choice of a particular protecting group will be determined generally by the conditions under which the thiazolidinone, metathiazanone, or derivative thereof is formed and by the types of protecting groups used on the side chains of the other components to be used in synthesis. In a most preferred embodiment, the protecting groups are photoremovable and their removal is accomplished by exposing the surface or selected regions thereof to light (e.g., from a light source through a mask) or removable under neutral conditions. Such protecting groups and techniques are described in U.S. Pat. No. 5,148,854 and co-pending U.S. patent applications Ser. No. 07/624,120, filed Dec. 6, 1990, and 07/971,181, filed Nov. 2, 1992.

The methods of the present invention can be utilized with sterically bulky amine components; however, it may be necessary to repeat the coupling process with fresh reagents, adjust the reaction temperature or concentrations of the other components, or otherwise use methods to drive the reaction to completion. For example, as discussed in Example 3 below, the condensation of valine, 0.25M benzaldehyde, and 0.5M mercaptoacetic acid proceeded in moderate yield (47%). A significantly improved yield (81%) was obtained by increasing the concentration of benzaldehyde to 1.0M and the concentration of mercaptoacetic acid to 2.0M.

D. The Carbonyl Component

A carbonyl component having the formula:

wherein $R^3$ and $R^4$ are independently selected from the groups consisting of hydrogen, alkyl, aryl, heteroaryl, carboxyl, carboxyalkyl, and arylalkyl is used in the described condensation reaction. Carbonyl components, if not commercially available, can be prepared by standard chemical procedures.

In a preferred embodiment, $R^4$ is not hydrogen. More preferably, $R^3$ is hydrogen and $R^4$ is not hydrogen and thus, the carbonyl component will comprise an aldehyde. A variety of aldehydes, including alkyl and aromatic aldehydes, optionally substituted, can be used. However, in some cases, the use of an aromatic aldehyde may be favored due to the increased stability of the product imine and thus, in a particularly preferred embodiment, $R^4$ is aryl or heteroaryl with the other being hydrogen. The potential racemization of the adjacent chiral center when the amino group comes from an amino acid may also be minimized with an aromatic aldehyde.

If the carbonyl component possesses reactive sites other than the carbonyl group, it may be necessary to protect them during the synthesis. As with the amine component, suitable protecting groups include acid-labile, base-labile, photoremovable, or removable under neutral conditions. See, e.g., Green, *Protecting Groups in Organic Synthesis*, Wiley 1985, pp. 218–288, which is incorporated herein by reference. The choice of a particular protecting group will be determined generally by the conditions under which the thiazolidinone, metathiazanone, or derivatives thereof is formed and by the types of protecting groups used on the side chains of the other components to be used in synthesis.

The carbonyl component typically will be utilized in a soluble form; however, it is within the scope of this invention to immobilize the aldehyde in a manner such that the carbonyl group is exposed. For example, a resin bearing an aromatic aldehyde (typically via coupling to the hydroxyl residue of a phenolic aldehyde), such as resin-bound 2-methoxy-4-oxyanisaldehyde, oxybenzaldehyde, or 4-oxyanisaldehyde, can be used as the carbonyl component. These resins can be made from commercially available resin backbones such as TentaGel S AC or TentaGel PHB by standard procedures apparent to those skilled in the art.

In a preferred embodiment, the amine component will comprise the limiting reagent and an excess of the carbonyl component will be used. Typically, the ratio of amine component to carbonyl component will range from about 1:1.1 to about 1:100, preferably from about 1:1.1 to about 1:25, and more preferably from about 1:1.1 to about 10.

E. The Thiol Component

The thiol component will comprise a mercapto carboxylic acid having the formula:

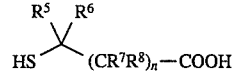

wherein $R^5$, $R^6$, $R^7$, and $R^8$ are independently selected from the groups consisting of hydrogen, alkyl, alkoxy, aryl, aryloxy, heteroaryl, carboxyl, carboxyalkyl, carboxyaryl, and arylalkyl and n is either 0 or 1 wherein n being 0 represents a valence bond. The thiol components, if not commercially available, can be prepared by literature procedures. See, e.g., Nicolet and Bate (1927) *J. Am. Chem. Soc.* 49:2064–2066 and Walsh et al. (1991) U.S. Pat. No. 5,061,720, each of which is incorporated herein for all purposes.

To prepare 4-thiazolidinones, an α-mercapto carboxylic acid is used and thus, n is zero. When the thiol component comprises a mercaptopropionic acid (i.e., n is one), a metathiazanone can be produced using the methods described herein. However, depending on the nature of the various components, the metathiazanone condensation may require the use of forcing conditions or additional rounds of coupling. Preferably, for the production of metathiazonones, the thiol component will comprise mercaptoproprionic acid, substituted mercaptopropionic acid, N-Ac-Cys-OH or N-Ac-penicillamine.

The thiol component typically will be utilized in a soluble form; however, it is within the scope of this invention to immobilize the thiol component in a manner such that the thiol group and the carboxyl group are available for reaction as shown below:

group can be coupled to a solid support, typically via the formation of an amide bond with a surface amino group. The thiol component is then deprotected with acid, typically TFA. Treatment of the immobilized thiol component with a carbonyl component and an amine component yields the corresponding thiaolidinone. Thus, in a particularly preferred embodiment, $R^5$ is hydrogen and $R^6$ is $CH_2COOH$ or $CH_2(CO)$-support (i.e., the carboxyl group has been covalently bound to the support). According to another preferred embodiment, an amine component comprising $R-NH_2$ or a salt thereof, wherein R is hydrogen, is used.

If the thiol component possesses reactive sites other than the mercapto group and the carboxyl group, it may be necessary to protect them during the synthesis. As with the amine component, suitable protecting groups include acid-labile, base-labile, photoremovable, or removable under neutral conditions. See, e.g., Green, *Protecting Groups in Organic Synthesis*, Wiley 1985, pp. 218–288, which is incorporated herein by reference. The choice of a particular protecting group will be determined generally by the conditions under which the thiazolidinone, metathiazanone, or derivatives thereof is formed and by the types of protecting groups used on the side chains of the other components to be used in synthesis.

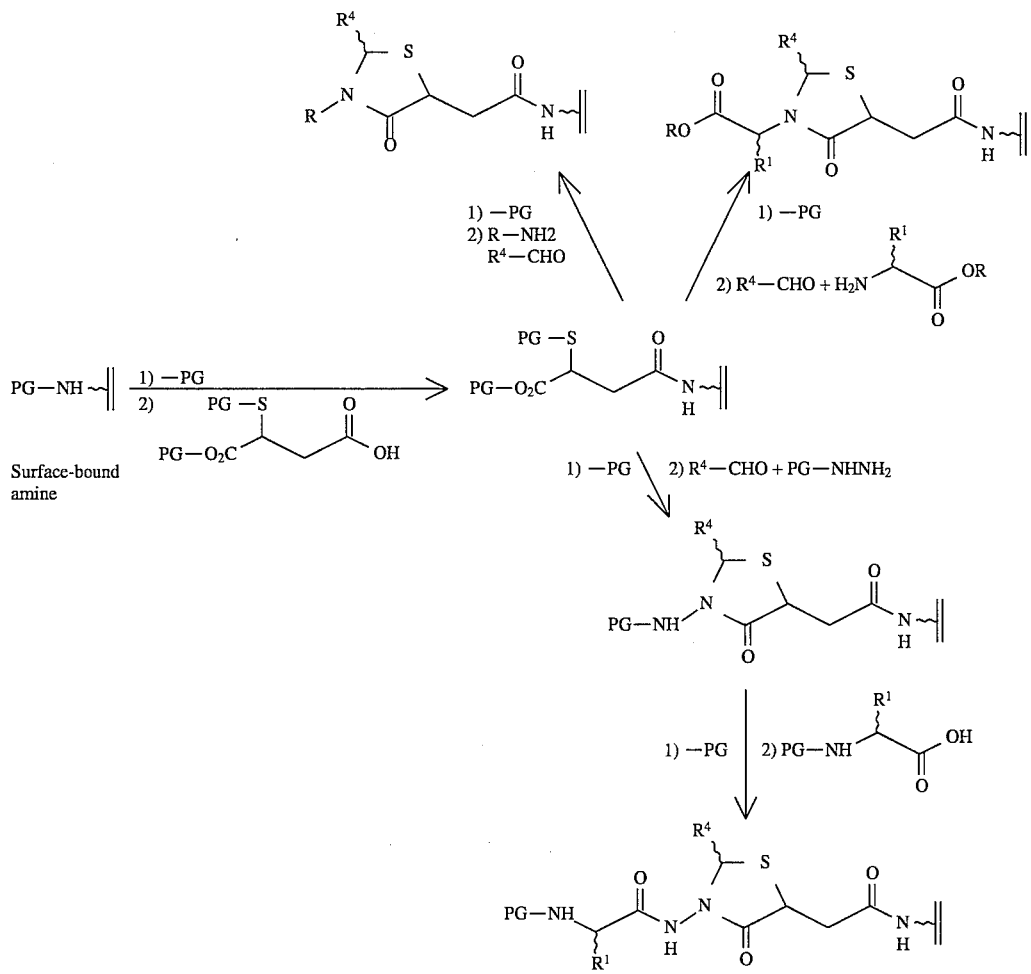

For example, pivaldehyde can be reacted with mercaptosuccinic acid to yield the corresponding protected thiol component having a free carboxyl group. This free carboxyl In a preferred embodiment, the amine component will comprise the limiting reagent and an excess of the carbonyl component will be used. Typically, the ratio of amine component to thiol component will range from about 1:1.1 to about 1:500, and preferably from about 1:1.1 to about 1:250.

F. The Exogenous Base

Often the condensation reaction is performed in the presence of an exogenous base. One equivalent of base liberates the salt of the amino acid when using commercial HCl salts or when employing N-Boc proctection and deprotecting with TFA. Preferably a slight excess of base is used. The ratio of amine component to exogenous base will range from about 1:1.1 to about 1:10, preferably from about 1:1.1 to about 1:5 and more preferably from about 1:1.1 to about 1:1.5. Optionally, one can neutralize the amine salt in a separate step prior to either imine or thiazolidinone (or metathiazanone or derivatives thereof) formation.

In a preferred embodiment, the exogenous base will be soluble in the reaction solvent. Particularly preferred exogenous bases include tri(lower alkyl)amines, such as diisopropylethylamine (DIEA) or triethylamine (TEA).

G. The Reaction Conditions

1. Immobilization

The reaction component that is first attached to the solid support surface will include a functionality that covalently binds the molecule to the solid support, e.g., activated carbonyl, acyl halide, or activated hydroxyl. The choice of functionality depends on the nature of the monomer and the type of solid support. Conditions for coupling through a wide variety of functional groups are known in the art. Typically the immobilized component will comprise either the amine component or the thiol component.

The active sites of the surface and/or the immobilized component are optionally protected initially by protecting groups which may be acid-, base-, or photoremovable protecting groups as discussed above. Among a wide variety of protecting groups are materials such as FMOC, BOC, t-butyl esters, t-butyl ethers, and the like. Various exemplary protecting groups are described in, for example, Atherton et al., *Solid Phase Peptide Synthesis*, IRL Press (1989), incorporated herein by reference and U.S. Pat. No. 5,148,854.

2. Reaction Temperature

The coupling reaction is generally performed at ambient conditions. However, depending on the nature of the various components, one of skill in the art will recognize that it may be necessary to perform the coupling at temperatures other than ambient. Typically, the coupling reaction can be accomplished between about 0° C. and 100° C.

3. Solvent

The condensation reaction is typically performed in an organic solvent, such as acetonitrile, tetrahydrofuran, methanol, or benzene, and preferably in a polar organic solvent. Most preferably, acetonitrile is used.

4. Dehydrating Agent

The condensation reaction is often performed in the presence of a dehydrating agent which in some embodiments, may serve to catalyze the condensation reaction. Preferred dehydrating agents include molecular sieves, magnesium sulfate, sodium sulfate, trimethyl orthoformate, zinc chloride, and the like. Most preferably, the dehydrating agent is in a form which can be easily washed away from the resin.

5. Stereochemistry

The condensation reaction typically yields a mixture of isomers. For example, according to HPLC analyses, the reaction with alanine or valine produced about a 2:1 mixture of isomers; whereas the reaction with phenylalanine gave about a 6:1 mixture. Typically, the relative proportions of the various diastereomers will reflect the steric demands of the amine and aldehyde components. The diastereomers (as the corresponding methyl ester derivative) generally can be separated quite readily via column chromatography. It should be noted, however, that extended exposure to base during the hydrolysis of the methyl ester of valine can result in racemization.

It will be recognized to those skilled in the arts that cyclocondensations often result in mixtures of stereoisomers and that reaction conditions such as temperature and solvent; the presence of catalysts, such as Lewis acids; and the like can be expected to alter the relative proportions of isomers formed in the condensation reactions. It may, for example, be possible to completely bias the outcome of a reaction to favor a single isomer or alternatively, to produce a mixture of isomers. It may also be possible to isomerize a mixture of thiazolidinones by treatment with elevated temperatures, catalysts, base, oxidizing agents, reducing agents, and the like. The particular application will govern whether one wishes to produce single isomers or mixtures. Libraries comprising stereoisomers can also be produced using the methods described herein.

6. Polymer Preparation

The condensation reaction can be performed once to yield a support-bound thiazolidinone, metathiazanone, or derivative thereof. Alternatively, the procedure can be repeated from two to about 20 times, preferably, from two to about 10 times, and more preferably, from about two to about 5 times, to yield a support-bound polymer having at least two thiazolidinone, metathiazanone, and/or derivative groups. This latter aspect of the invention will find use particularly in the preparation of peptidomimetics as discused below.

H. Preparation of Derivatives of Thiazolidinones and Metathiazonones

The thiazolidinone (or metathiazonone) ring system can be further manipulated as shown below:

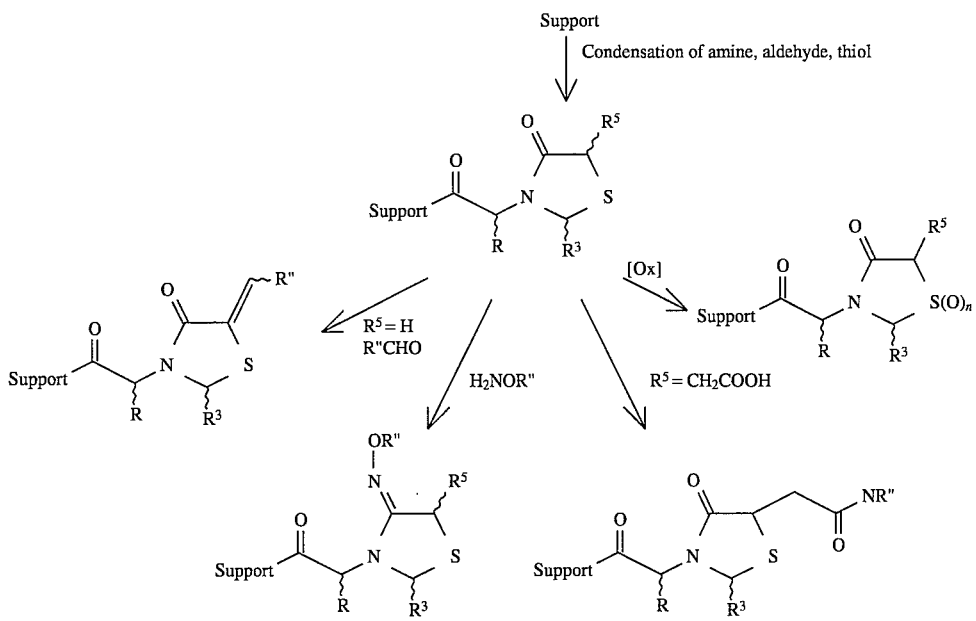

For example, the sulfur atom can be oxidized to either the sulfoxide or sulfone. See, e.g., Fuchigami et al. (1992) *J. Org. Chem.* 57:3755–3757 and Walsh and Uwaydah (1991) U.S. Pat. No. 5,061,720. Heating of the corresponding sulfone should affect the expulsion of $SO_2$ and the formation of the corresponding β-lactam. See, e.g., Fuchigami et al. (1992) *J. Org. Chem.* 57:3755–3757.

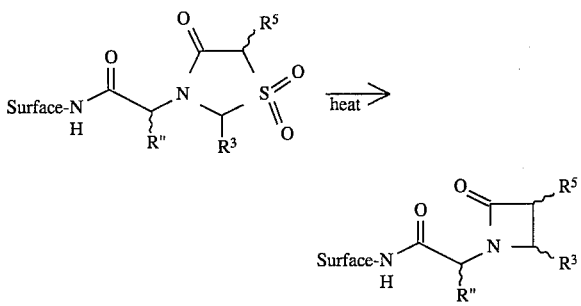

Alkylidene derivatives can also be produced by the reaction of a thiazolidinone ring having no substitution on the 5 position of the ring with an aldehyde. See, e.g., Harhash et al. (1973) *Ind. J. Chem.* 11:128–130. Alternatively, 5-alkylidene derivatives can be prepared directly by condensing the corresponding alkylidene-mercaptoacetic acid with the appropriate amine and carbonyl components.

The carbonyl group of the thiazolidinone ring system is also amenable to further derivitization. For example, thiazolidinones can be reacted with hydroxyl amine to generate the corresponding 4-oximyl derivative. See, e.g., Diurno et al. (1992) *J. Med. Chem.* 35:2910–1912. Likewise, the thiazolidinone ring can be treated with a substituted hydazine to provide a source of further diversity.

Additionally, if further functionality is present on $R^1$, $R^2$, $R^3$, $R^4$, $R^5$, or $R^6$, this functionality can be modified. For example, if $R^5$ (or another of the substituents) is —$CH_2COOH$ (i.e., the thiol component is mercaptosuccinic acid which is commercially available from Aldrich Chemical Company, Milwaukee, Wis.), then this acid functionality may be further reacted with a variety of amines, thiols, alcohols, and the like to produce amides, thioesters, esters, etc. Techniques for the further manipulation of a support-bound carboxyl group are known in the art and can be found in copending U.S. application Ser. Nos. 08/201,607, filed Feb. 25, 1994, and 08/179,741, filed Jan. 11, 1994, each of which is incorporated herein by reference. Alternatively, if $R^5$ (or another of the substituents) is an amino group (i.e., the thiol component is isocysteine, see Gustavson and Srinivasan (1991) *Syn. Comm.* 21:265–270), the corresponding thiazolidinone could be derivatized with a variety of isocyanates, carboxylic acids, amino acids, and the like using techniques known in the art.

The above examples are illustrative; other transformations, such as alkylations, acylations, and the like, will be apparent to those skilled in the art. For purposes of simplicity, the amine-bound thiazolidinone is shown; however, the corresponding carbonyl or thiol-bound thiazolidinones could also be further derivatized.

I. Cleavage

For some applications, one may desire a "support-free" or "soluble" library of molecules. Soluble molecules, both tagged and untagged, can be useful for a variety of purposes, including assaying the activity of a compound and structural analysis. The generation of soluble molecular libraries, both tagged and untagged, and the solubilization of compounds, both tagged and untagged, synthesized on a solid support can be accomplished by techniques known in the art.

Typically, cleavable linkers such as those described in U.S. Ser. No. 978,940, filed Nov. 19, 1992, incorporated herein by reference can be employed. To produce a soluble tagged molecule, the cleavable linker will be attached to the bead or other solid support and have at least two functional groups: one for synthesizing the molecule of interest and the other for synthesizing the tag. Thus, the molecule and tag can be synthesized attached to a common linker, which, in turn, is bound to the solid support. Once the molecule and tag are synthesized, the linker is cleaved to provide a soluble tagged molecule Reversible covalent linkages can be used to attach the tagged molecules to the support. Examples of suitable reversible chemical linkages include (1) a sulfoester linkage provided by, e.g., a thiolated tagged-molecule and a N-hydroxysuccinimidyl support, which linkage can be controlled by adjustment of the ammonium hydroxide concentration; (2) an benzylhydryl or benzylamide linkage provided by, e.g., a Knorr linker, which linkage can be controlled by adjustment of acid concentration; (3) a disulfide linkage provided by, e.g., a thiolated tagged-molecule and a 2-pyridyl disulfide support (e.g., thiolsepharose from Sigma), which linkage can be controlled by adjustment of the DTT (dithiothreitol) concentration; and (4) linkers which can be cleaved with a transition metal (i.e. HYCRAM).

The linker may be attached between the tag and/or the molecule and the support via a non-reversible covalent linkage. For example, linkers which can be cleaved photolytically can be used. Preferred photocleavable linkers of the invention include 6-nitroveratryoxycarbonyl (NVOC) and other NVOC related linker compounds (see PCT patent publication Nos. WO 90/15070 and WO 92/10092; see also U.S. patent application Ser. No. 07/971,181, filed 2 Nov. 1992, incorporated herein by reference); the ortho-nitrobenzyl-based linker described by Rich (see Rich and Gurwara (1975) *J. Am. Chem. Soc.* 97:1575–1579; and Barany and Albericio (1985) *J. Am. Chem. Soc.* 107: 4936–4942) and the phenacyl based linker discussed by Wang. (see Wang (1976) *J. Org. Chem.* 41:3258; and Bellof and Mutter (1985) *Chimia* 39:10). Other particularly preferred photocleavable linkers are shown below:

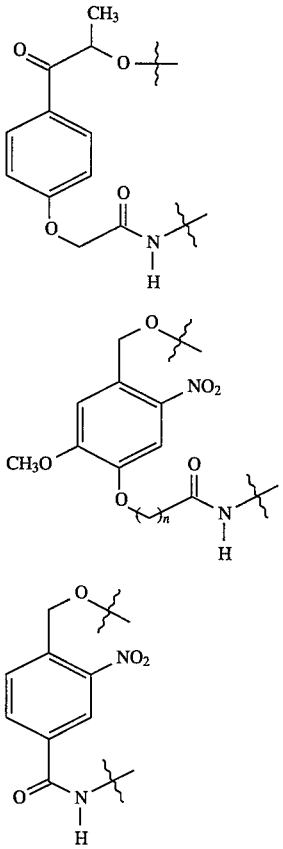

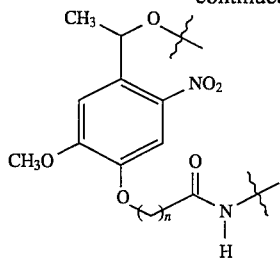

In another embodiment, the linkers are nucleic acids with one or more restriction sites, so that one portion of a library member (either the tag, the compound of interest or both, or the solid support) can be selectively cleaved from another by the appropriate restriction enzyme.

In addition, various linkers can be cleaved from the thiazolidinones or derivatives thereof via the action of a nucleophile (i.e., a group that is capable of donating or sharing its electrons). Examples of a linker which would be amenable to this type of cleavage mechanism are shown below:

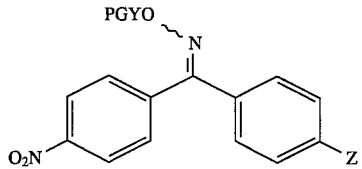

where Y is carbonyl and Z is a reactive site selected from the group of halogen (i.e., in a halo alkyl), O, NHS, S—$(CH_2)_nO$, and $NHCO(CH_2)_nCO_2$. Tethers of this type can be derived from commercially available resins, such as those available from Novabiochem, using techniques known in the art.

These tether molecules are particularly sensitive to nucleophilic attack. Treatment of the resin with a nucleophile, such as hydroxide ion, ammonia, alkyl amines, thiois, or hydrazine, affords cleavage of the immobilized thiazolidinones and regenerates the oxime moiety of the resin. Significantly, selection of the appropriate nucleophile allows for the generation of additional diversity. For example, cleavage with a variety of alkyl amines would generate the corresponding alkyl carboxamide analogs.

J. Analysis of the Thiazolidinones

The extent of completion of the condensation reaction and the nature of the thiazolidinone product can be ascertained using various procedures. For example, high-resolution gel phase $^{13}C$ NMR spectroscopy can be used to monitor the progress of a reaction and/or to identify the product. In addtion, changes in hybridization and electron density can be easily monitored using this technique with little interference from solvent or other non-labeled sites.

A $^{13}C$ label is incorporated into at least one of the components. The label typically will be incorporated into the amine or carbonyl component because of the commercial availability of these compounds. However, one of skill in the art will readily appreciate that the other components could also be labeled. Resins and linkers which do not have absorbances in the regions of interest should be used. Preferably, a polystyrene resin, such as TentaGel, and a polyethyleneglycol (PEG) linker, is used. Polystyrene resins tend to be $^{13}C$-invisible and the linker often will exhibit a single sharp resonance at about 70 ppm.

The use of this technique is exemplified in FIG. 1. $^{13}C$-labeled glycine (the label is indicated with a "*") was coupled to TentaGel resin with a PEG linker. The support-bound amine component exhibited a sharp resonance at about 43 ppm as shown in Panel D of FIG. 1. The support-bound amine was treated with benzaldehyde to yield the corresponding imine. The reaction proceeded almost quantitatively as shown by the disappearance of the amine resonance and the appearance of a resonance at 64 ppm which can be attributed to the imine. See Panel C of FIG. 1. The imine could be converted back to the amine by treatment with acetic acid. See Panel B of FIG. 1. Treatment of the imine with mercaptoacetic acid afforded the thiazolidinone which exhibited a resonance at about 45 ppm as shown in Panel B of FIG. 1.

Figures 2A, 2B, 2C:
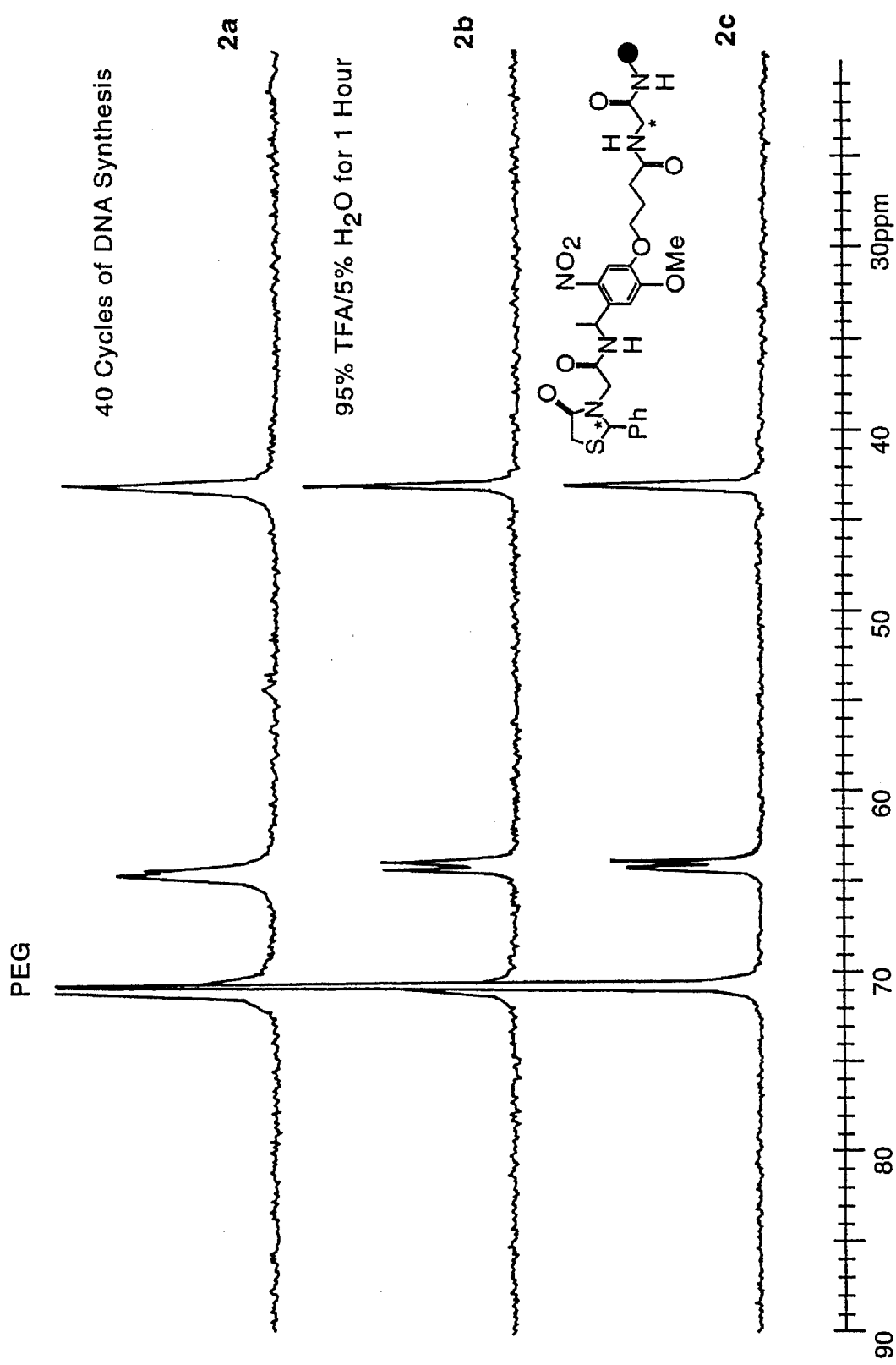
FIG. 2 illustrates the use of $^{13}C$ NMR to monitor the stability of thiazolidinones. Panel C shows the $^{13}C$ NMR spectrum of support-bound thiazolidinone which has been doubly labeled with a $^{13}C$-atom at the position 2 of the ring and at the position alpha to the carbonyl of the linker (labeled positions are indicated with a "*"). Panel B shows the $^{13}C$ NMR spectrum of support-bound doubly labeled thiazolidinone after treatment with 95% TFA for one hour. Panel A shows the $^{13}C$ NMR spectrum of support-bound doubly labeled thiazolidinone after 40 cycles of DNA synthesis.
Figures 3A, 3B, 3C:
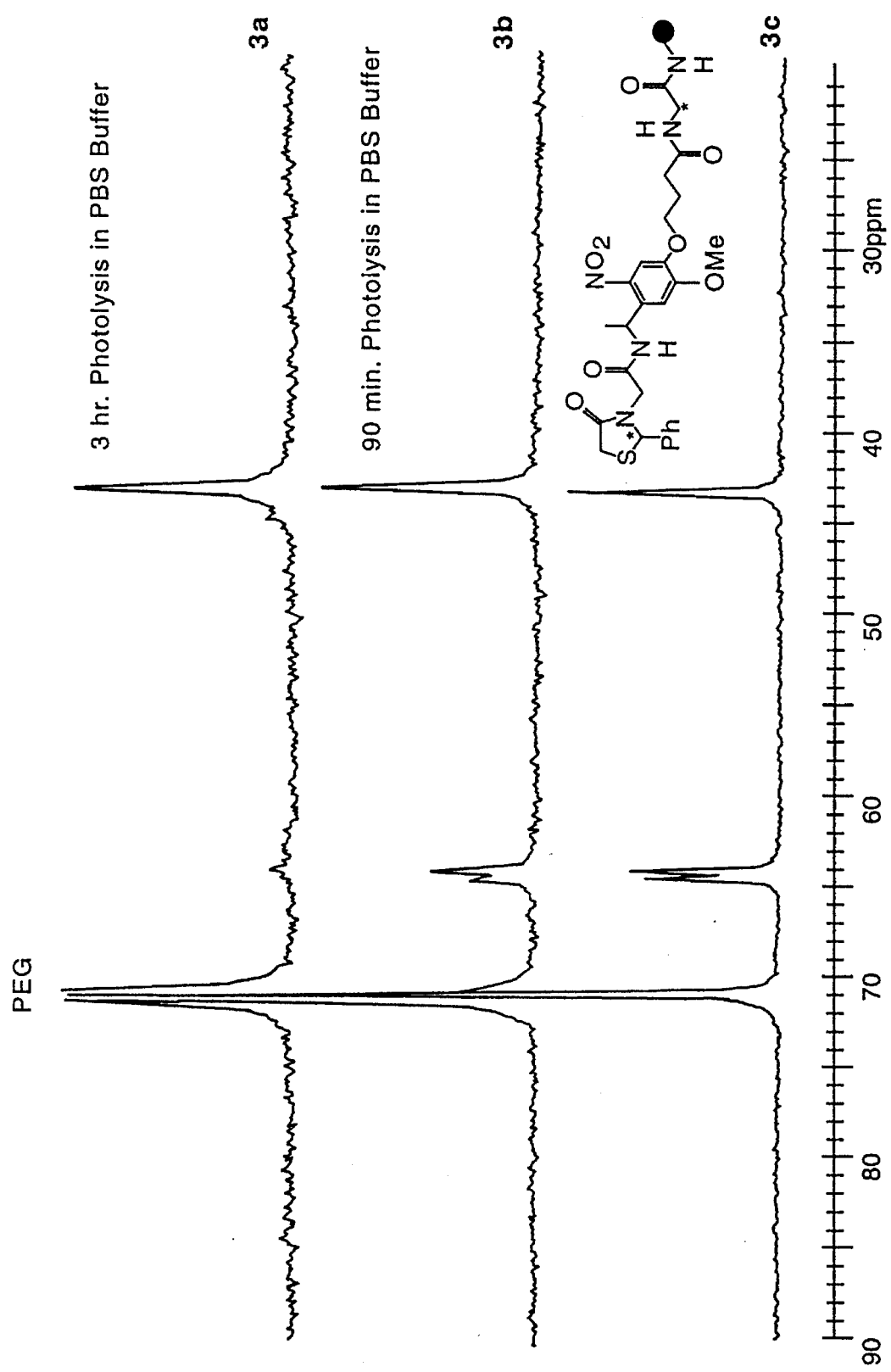
FIG. 3 further illustrates the use of $^{13}C$ NMR to monitor the stability of thiazolidinones. Panel C shows the $^{13}C$ NMR spectrum of support-bound thiazolidinone which has been doubly labeled with a $^{13}C$-atom at the position 2 of the ring and at the position alpha to the carbonyl of the linker (labeled positions are indicated with a "*". Panel B shows the $^{13}$C NMR spectrum of support-bound labeled thiazolidinone after 90 minute photolysis in PBS buffer. Panel A shows the $^{13}$C NMR spectrum of support-bound labeled thiazolidinone after 3 hours of photolysis in PBS buffer.
Figure 4:
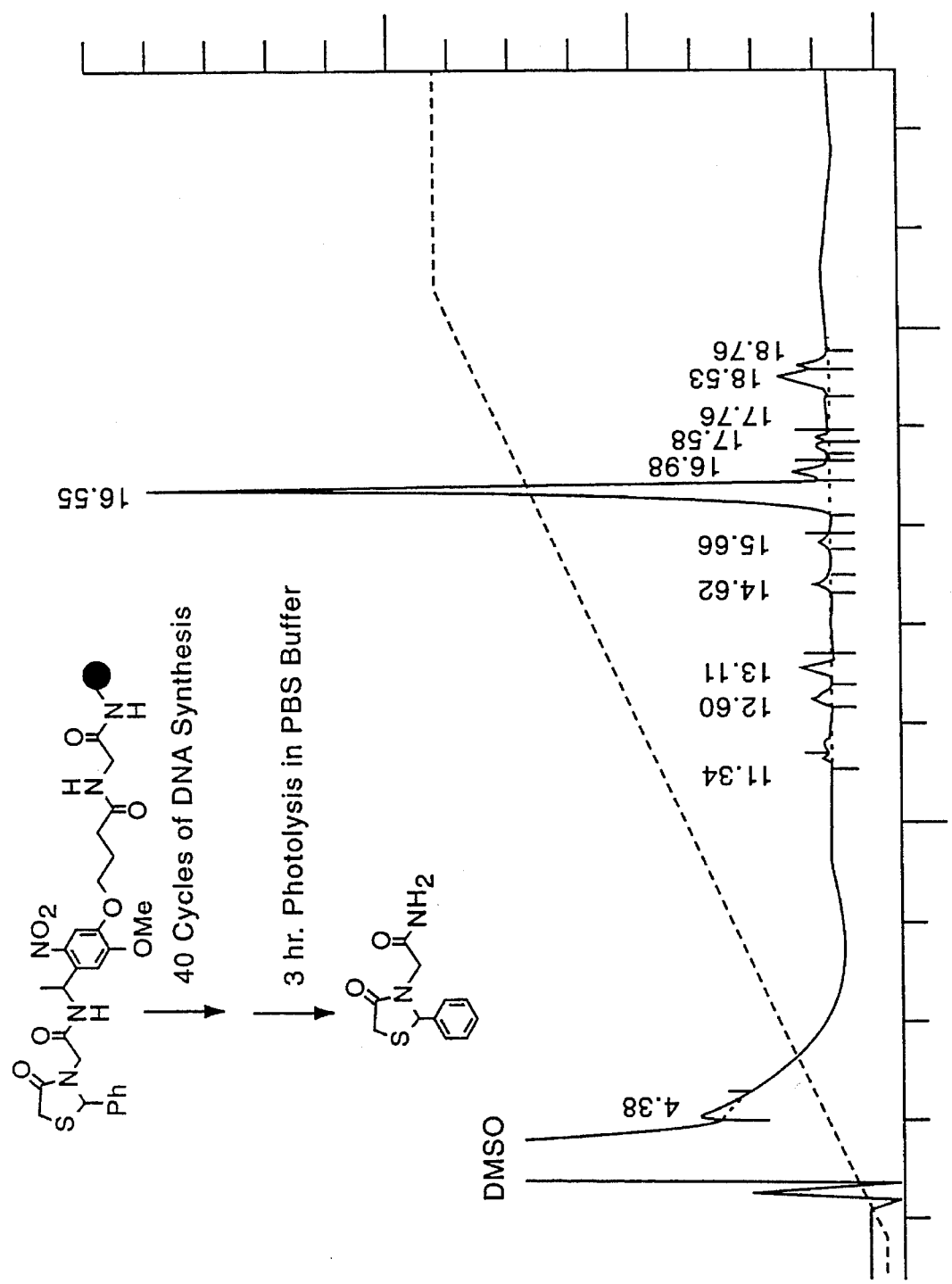
FIG. 4 shows an HLPC trace for the reaction mixture produced by subjecting a support-bound thiazolidinone to 40 cycles of DNA synthesis and 3 hour photolysis in PBS buffer.

A further example of the use of $^{13}$C NMR to perform stability studies is shown in FIGS. 2 and 3. Specifically, Panel C of FIG. 2 (or FIG. 3) shows a $^{13}$C NMR spectrum of a support-bound thiazolidinone with a sharp peak at about 43 ppm attributable to the labeled carbon. As shown in Panels A and B of FIG. 2, additional resonances did not appear when the support-bound thiazolidinone was subjected to acid treatment, of the conditions typically used in DNA synthesis (e.g., the conditions used to introduce an oligonucleotide tag, that is, alternating rounds of mild acid treatment, exposure to phosphoramidites, and mild oxidation conditions), thus demonstrating that thiazolidinones are stable to these conditions. See also, FIGS. 4 and 6 and discussion below.

Photolysis afforded cleavage of the thiazolidinone from the support. Further photolysis did not effect the $^{13}$C resonance. See Panels A and B of FIG. 3. The support-bound thiazolidinone which had been subjected to 40 cycles of DNA synthesis was also cleaved from the support and analyzed by HPLC. Significantly, the HPLC trace showed the presence of the correct thiazolidinone product. See FIG. 4.

Also, as discussed in detail below, techniques are available which allow for the cleavage of a portion of the support-bound thiazolidinones while leaving the remainder of the support-bound molecules intact. In addition to the assay procedures described below, these techniques will find use in the structural analysis and identification of thiazolidinones. Specifically, a library of thiazolidinones, metathiazanones, and derivatives thereof is assayed using procedures known in the art and a first population of the libary is selected as having desirable characteristics. This first population of these support-bound molecules can be subjected to cleavage conditions such that only a portion of the molecules are cleaved from the support. The cleaved material can be isolated and analyszed using conventional techniques, preferably mass spectroscopy. As many, if not all, of the members of the library will have distinctive molecular weights or other physical characteristics, the identity of the desirable molecules can be ascertained from the analyses. Thus, in certain circumstances, it will not be necessary to "tag" the molecules. The thiazolidinones, by virtue of their molecular weight characteristics, can serve as "self-tags".

III. Preparation of Arrays of Thiazolidinones

A. General Overview

The methods described above may be used to prepare and screen large numbers of compounds, in the hundreds, the thousands and even the ten thousands in a reasonable period of time. Synthesis may be combined with screening in various different ways to screen compounds in unusually large libraries. Preferably, the techniques described above are used to synthesize more than 2, preferably more than 5, preferably more than 10, more preferably more than 50, more preferably more than 100, and more preferably more than 1,000 different molecules simultaneously.

Significantly, the methods described herein can be utilized in a stepwise fashion as well as in a one-step condensation reaction, thus drastically decreasing the number of reactions required for the preparation of an array. For example, assuming that 36 different nitrogen sources, 36 different aldehydes, and 36 different thiol components are available as building blocks, then 1332 reactions would be required (i.e., 36 reactions to couple the first component to the support, followed by 1296 condensation reactions) to prepare the arrays using a one-pot condensation. However, if a stepwise procedure is followed wherein one component is coupled to the support, followed-up by condensing one component to the immobilized component, and then by adding the final component, only 108 reactions (i.e., 3×36 individual couplings) are required to prepare the same array. This is shown schematically in FIG. 5. That is, the ability to repool the imine-containing resin allows one to dramatically reduce the total number of manipulations/steps/reactions vessels necessary to generate the complete library. Thus, the ability to couple the components stepwise, rather than in a one-pot protocol, dramatically increases the efficiency of library production by reducing the number of reactions required to produce the array.

The invention provides for the use of solid support(s) on which the chemical coupling steps are conducted. The solid support includes a plurality of spatially addressable regions, for example, beads, pins, cavities or wells, and the like. The solid support is optionally provided with linker molecules having active sites as discussed above. The active sites are optionally protected initially by protecting groups. In some embodiments, the linker molecule may provide for a cleavable function by way of, for example, exposure to acid, base, or light.

In an initial step, one or more of the regions of the solid support are activated by removal of the protecting groups, if present. It will be recognized that in some embodiments, regions may be activated simultaneously. Alternatively, the regions may be individually activated. In the particular case of acid labile protecting groups, such activating agents may include acid, while in the case of base labile groups, such agents may include base.

Thereafter, a first portion of a molecule to be synthesized is added to the support, for example, the first portion will typically be a substituted amino acid linked to the support via the carboxyl group. The amino group and the side chain functionality of the amino acid may be protected by an appropriate protecting group. Alternatively, the first portion will comprise the thiol component. The mercapto group and the carboxyl group may be protected with appropriate protecting groups. In other embodiments, the first portion will comprise the carbonyl component. The protecting group(s), if any, on the immobilized component may be the same as or different from the protecting group on the solid support. In most cases, the various regions will be coupled to different molecules.

Due to the presence of protecting groups on the reactive sites, undesirable coupling will not take place in the protected regions. The second and third components are then introduced to the immobilized component, typically in a sequentially order, and the condensation reaction is affected. It will be recognized by those of skill in the art that additional steps of washing and the like will be desirable in some embodiments. Subsequent modifications of the thiazolidinone or metathiazanone ring structure or cleavage of the compounds from the support can then occur.

The synthesis of combinatorial chemistry libraries can be characterized in terms of complexity. For example, as discussed above, the "pure" stepwise procedure using a plurality of amine components, a plurality of thiol components, and a plurality of carbonyl components in each coupling reaction with mixing and apportioning steps between each component addition generates all possible compounds in the fewest number of steps.

An alternative synthetic format is based on the "one-step" procedure described above. Specifically, a plurality of amine components, a plurality of thiol components, and a plurality of carbonyl components are used. However, the supports are not mixed between the addition of at least one component. This format generates all possible compounds; however, additional steps are needed. This format will find utility for the preparation of authentic samples or for follow-up experiments (i.e., the preparation of secondary libraries based on an initial lead structure).

A third format calls for the use of additional reaction steps. For example, a single carbonyl component can be reacted with a plurality of support-bound amine components, wherein each of the different amine components is in a predefined region. Likewise, a plurality of support-bound imines, wherein each of the different imines is in a predefined region, can be condensed with a single thiol component. This format allows one to examine the effect of reaction conditions and/or stoichiometry of the reagents on product yield and purity.

B. Preparation of Encoded Libraries

1. Overview

As one example of a strategy for a large library, the scheme may begin by the preparation of an approximately equimolar mixture of a variety of amino acids to which a common linker is attached. In a preferred embodiment, the monomers are bound to resin beads, and the compounds are constructed using a stochastic method of polymer synthesis as described in co-pending U.S. patent application Ser. No. 07/946,239, filed Sep. 16, 1992; Ser. No. 07/762,522, filed Sep. 18, 1991; Ser. No. 08/146,886, filed Sep. 2, 1993; Lam et al. (1991) Nature 354:82–84; PCT application no. 92/00091 and Houghten et al., (1991) Nature 354:84–86, each of which is incorporated herein by reference for all purposes.

A large plurality of beads are suspended in a suitable carrier (such as a solvent) in a parent container. The beads are provided with optional linker molecules having an active site. The active site is protected by an optional protecting group. In a first step of the synthesis, the beads are divided for coupling into separate containers. If present, the protecting groups are then removed and a first portion of the molecule to be synthesized is added to the various containers. For example, the first portion of the molecule to be synthesized may be various optionally protected substituted amino acids, represented herein by $A_n$, $A_1$, $A_2$, and $A_3$, which have been coupled to the surface via their carboxyl groups.

Thereafter, the various beads are washed of excess reagents as appropriate, and remixed in the parent container. Again, it will be recognized that by virtue of the large number of beads utilized at the outset, there will similarly be a large number of beads randomly dispersed in the parent container, each having a particular first portion of the monomer to be synthesized on a surface thereof.

Thereafter, the various beads are again divided for coupling in the separate containers. The beads in the first container are exposed to a second portion of the molecule to be synthesized, represented by $B_1$, while the beads in the second and third containers are coupled to molecule portions $B_2$ and $B_3$ respectively. Typically, the immobilized amino acids will be treated with a selection of aldehydes. Accordingly, imines $A_1B_1$, $A_2B_1$, and $A_3B_1$ will be present in the first container, while $A_1B_2$, $A_2B_2$, and $A_3B_2$ will be present in the second container, and molecules $A_1B_3$, $A_2B_3$, and $A_3B_3$ will be present in the third container. Each bead, however, will have only a single type of molecule on its surface. In the particular embodiment described herein, all of the possible molecules formed from the first portions $A_1$, $A_2$, $A_3$, and the second portions $B_1$, $B_2$, and $B_3$ have been formed.

Optionally, the beads are then recombined into the parent container, mixed, and divided again in the separate conditions. The beads in the first container are then exposed to a third portion of the molecule to be synthesized, represented by $C_1$, while the beads in the second and third containers are coupled to molecule portions $C_2$ and $C_3$ respectively. Typically, the third portion of the molecule to be synthesized will the thiol component. Accordingly, molecules $A_1B_1C_1$, $A_2B_1C_1$, and $A_3B_1C_1$ will be present in the first container, while $A_1B_2C_2$, $A_2B_2C_2$, and $A_3B_2C_2$ will be present in the second container, and molecules $A_1B_3C_3$, $A_2B_3C_3$, and $A_3B_3C_3$ will be present in the third container. Each bead, however, will have only a single type of molecule on its surface. In the particular embodiment described herein, all of the possible molecules formed from the various first, second, and third portions have been formed.

Additional steps such as alkylation, oxidation of the sulfur atom, and the like as discussed below can be conducted on the condensation products.

2. The Identifier Tag

According to some embodiments, the solid support will bear an identifier tag. The identifier tag has a recognizable feature that is, for example, microscopically or otherwise distinguishable in shape, size, mass, charge, or color. This recognizable feature may arise from the optical, chemical, electronic, or magnetic properties of the tag, or from some combination of such properties. In essence, the tag serves to label a molecule and to encode information decipherable at the level of one (or a few) molecules or solid supports. By using identifier tags to track the synthesis pathway that each member of a chemical library has taken, one can deduce the structure of any chemical in the library by reading the identifier tag. Particularly preferred identifier tags include synthetic oligodeoxyribonucleotides. For further detail on identifier tags, see U.S. patent application Ser. No. 08/146, 886 and Ser. No. 08,149,675. An example of a parallel synthesis of a thiazolidinone with an oligonucleotide tag is shown in FIG. 6 and described further below.

The identifier tags identify each reaction step that an individual library member or solid support has experienced and record the step in the synthesis series in which each chemical reaction was performed. The tags may be added immediately before, during, or after the chemical reaction, as convenient and compatible with the type of identifier tag, modes of attachment, and chemistry of molecular synthesis.

As shown herein, thiazolidinones are stable to light, DNA synthesis, and treatment of TFA. In addition, by varying the substituents, a set of compounds having unique molecular weights can be designed. Thus, the thiazolidinone, metathiazanone, or derivative thereof can find utility as an identifier tag. After cleavage, the tags can be analyzed using mass spectroscopy or other means of physical characterization. As described more fully below, techniques are available for cleaving just a portion of the support-bound molecules from the support while leaving the remainder of the support-bound molecules intact. Thus, thiazolidinones can serve as tags to identify other small molecules (e.g., diketopiperazines, pyrollidines, benzodiazepines, and the like), peptides or DNAs.

C. Preparation of Arrays using the VLSIPS™ Technique

The VLSIPS™ technique also can be used to construct a library of thiazolidinones for screening with various active substances (see U.S. Pat. No. 5,143,854), and the compounds are screened while still immobilized or attached to the solid support. Regions of a glass solid support provided with protecting groups, optionally coupled to the solid support via linker molecules, typically photoprotected amines, are exposed to light shone through a mask to form regions of free and protected amines. The protecting groups are removable upon exposure to light. Accordingly, the protecting groups in a first selected region are removed by exposing the first selected region to light, but not exposing the second selected region to light. This selective irradiation step may be accomplished through the use of a mask such as the masks commonly used in the semiconductor industry. Such techniques are described in greater detail in U.S. Pat. No. 5,143,854 (Pirrung et al.), incorporated herein by reference for all purposes.

A first set of amine components, typically amino acids with appropriate light, base, or acid labile protecting groups, is then introduced to the solid support such that the carboxyl group of the amino acid is bound to the surface. The amine component is then treated with at least one aldehyde and then at least one thiol component under conditions suitable to afford the desired condensation product. After washing to remove excess reagents and byproducts, the array can be further derivatized using additional steps of photolysis to remove protecting group(s) in a second region followed by reaction with other aldehydes and thiols. This procedure can be repeated to produce the desired array of thiazolidinones, etc. The resulting thiazolidinones, metathiazanones, and derivatives can be assayed using the procedures described below.

In a similar manner to that described above, the solid support is then exposed to a receptor of interest that is appropriately labeled with, or coupled to another receptor with a label, such as a fluorescent or radioactive label. The solid support is then scanned to determine the location of the label. From knowledge of the composition of the molecule synthesized at each site, it becomes possible to identify the molecule(s) that are complementary to the receptor.

D. Other Methods

Arrays also can be prepared using the pin approach developed by Geysen et al., for combinatorial solid-phase peptide synthesis. A description of this method is offered by Geysen et al., *J. Immunol. Meth.* (1987) 102:259–274, incorporated herein by reference. According to this method as it may be practiced in the present invention, a series of 96 pins are mounted on a block in an arrangement and spacing which correspond to a 96-well Microtiter reaction plate, and the surface of each pin is derivatized to contain terminal aminomethyl groups. The pin block is then lowered over a series of reaction plates in sequence to immerse the pins in the wells of the plates where coupling occurs at the terminal aminomethyl groups and the various reactions in the reaction schemes described above are performed.

Reagents varying in their substituent groups occupy the wells of each plate in a predetermined array, to achieve as ultimate products a unique thiazolidinone or derivative on each pin. By using different combinations of substituents, one achieves a large number of different compounds with a common central thiazolidinone and/or metathiazanone structure. Once formed in this manner, each derivative may be cleaved from its pin by treatment with acid, as described above.

E. Instrumentation

The methods of the present invention are readily automated using technology presently available for binding and reacting monomers to form polymer chains and removing the byproducts of those reactions. Moreover, the methods described herein are amenable to the simultaneous production of a variety of different thiazolidinones, metathiazanones, or derivatives thereof.

An apparatus capable of preparing arrays of 4-thiazolidinones, metathiazonones, and derivatives thereof is described in U.S. patent application Ser. No. 08/149,675, filed Nov. 2, 1993, incorporated herein by reference. Such an instrument is capable of performing up to 100 or more parallel reactions simultaneously by distributing the reaction mixture or slurry of synthesis solid supports, under programmable control, to the various channels for pooling, mixing, and redistribution.

Another apparatus capable of preparing arrays according to the methods described herein is described in association with the synthesis of peptides in Geysen et al., *J. Immun. Methods* (1987) 102:259–274, incorporated herein by reference for all purposes. In brief, this method utilizes a solid support having a plurality of pins or other extensions. The pins are each inserted simultaneously into individual reagent containers in tray. Although in a common embodiment, an array of 96 pins/containers is utilized, it will be recognized that in other embodiments a larger array of such pins/containers will be provided. Each tray is filled with a particular reagent for coupling in a particular chemical reaction on an individual pin. Accordingly, the trays will often contain different reagents. Since the chemistry disclosed herein has been established such that a relatively similar set of reaction conditions may be utilized to perform each of the reactions, it becomes possible to conduct multiple chemical coupling steps simultaneously.

Other instruments amenable for use with the methods described herein are commercially available. For example, robotic systems, such as that available from Advanced Chemtech, and other non-pin based instruments can be utilized.

IV. Utility

A. Thiazolidinones and Derivatives as Peptidomimetics

The compounds prepared by the methods described herein are similar in structure to dipeptides in that the compounds prepared herein have similar length, distribution of side chain functionality and general bonding features inherent in dipeptides as shown in FIG. 7. The constructed mimetics can be further elaborated with additional amino acids being coupled to either side of the mimetic and can thus, the thiazolidinone or metathiazanone group can be located at any position within a peptide sequence. Thus, these classes of compounds can serve as peptidomimetics and should find utility in ligand optimization and drug discovery programs involving peptidic leads.

B. Thiazolidinones and Derivatives As Therapeutics

In addition, as discussed above, specific members within the class of compounds have been shown to have antifungal, antihistaminic, or antimicrobial activity and have been uses in the treatment of inflammation, hypertension, renal failure, congestive heart failure, uremia and other conditions. According to a particularly preferred embodiment of this invention, a mixture of primary amines, aldehydes, and/or a mixture of α-mercapto carboxylic acids and/or a mixture of β-mercapto carboxylic acids are used to produce a library or array of solid support-bound thiazolidinones, metathiazanones, or derivatives thereof. These libraries will find use in the identification of novel thiazolidinones, metathiazonones, and derivatives thereof with various therapeutic properties, including but not limited to those listed above.

V. Assays

Since a wide array of substituted amino acids, aldehydes, and thiol components are readily available, the synthesis technique herein results in an array of immobilized materials which are at known locations on the solid support or in a soluble format and may be effectively used in screening studies to determine which of the synthesized materials show significant affinity for a receptor or receptors of interest. Receptor affinity can be studied by exposing the solid support to the receptor or receptors of interest, and determining where the receptor has bound to the solid support. In some embodiments, the location of the receptor on the solid support may be conveniently located by labeling the receptor with an radioactive or fluorescent label, and scanning the surface of the solid support for the presence of the receptor. In some embodiments, the receptor of interest may be unlabeled, but later exposed to a second receptor that is labeled and known to be complementary to the receptor of interest. The receptor will bind to the molecules that are complementary to the receptor while it will not bind to other molecules on the solid support. Accordingly, the present method provides an effective way to identify ligands that are complementary to a receptor.

In a particularly preferred embodiment, the solid support comprises beads and the receptor is fluorescently or radioactively labeled. Thereafter, one or more beads are identified that exhibit significant levels of, for example, fluorescence using one of a variety of techniques. For example, in a preferred embodiment, fluorescence activated cell sorting (FACS) is used to select for those beads having selected levels of fluorescence. In another embodiment, mechanical separation under a microscope is utilized. The identity of the molecule on the surface of such separated beads is then identified using, for example, NMR, mass spectrometry, or the like.

In alternative embodiments the identity of the molecule that is complementary to the receptor is determined with respect to the "bin" or container in which the labeled receptor is located. For example, by exposing the molecules in the various containers to the labeled receptor, the identity of one terminal portion of the molecule may be identified. For example, if fluorescence is noted after exposure to the molecules in the first container, but not in the second or third containers, it is readily determined that the molecule that produces a complementary receptor is having the building block introduced in the first container as opposed to those molecules having the building blocks introduced in the second or third containers. Thereafter, one will synthesize all of the molecules having the "active" building block in separate containers. The identity of the other active portions of the molecule can then be determined by identifying where receptor binding is located among these molecules.

One can also employ molecular libraries to useful effect in novel assays of the invention in which a ligand is solubilized in either tagged or untagged form prior to binding to a receptor of interest. For screening very large libraries of soluble tagged libraries, one preferably employs affinity chromatography under conditions of weak affinity.

Soluble molecules can also be screened using an immobilized receptor. After contacting the molecules with the immobilized receptor, and washing away non-specifically bound molecules, bound molecules are released from the receptor by any of a wide variety of methods. The tags, if present, are optionally amplified and then examined and decoded to identify the structure of the molecules that bind specifically to the receptor. A tagged molecule in solution can be assayed using a receptor immobilized by attachment to a bead, for example, by a competition assay with a fluorescently labeled ligand. The beads bearing immobilized receptors can be recovered and the sorted using FACS to identify positives (diminished fluorescence caused by the library molecule competing with the labeled ligand).

The soluble molecules of the library can be synthesized on a solid support and then cleaved prior to assay. In one embodiment, microscopic beads of a molecular library are placed in very small individual compartments or wells that have been "nanofabricated" in a silicon or other suitable surface. Beads are loaded into the wells by dispersing them in a volume of loading buffer sufficient to produce an average of one bead per well. In one embodiment, the solution of beads is placed in a reservoir above the wells and the beads are allowed to settle into the wells. Cleavage of the molecules from the beads may be accomplished using chemical or thermal systems, but a photocleavable system is preferred. The molecules of interest can be cleaved from the beads to produce either untagged molecules in solution (the tag remaining attached to the bad) or tagged molecules in solution. In either event, the molecules of interest are cleaved from the beads but remain contained within the compartment along with the bead and the identifier tag(s).

In another embodiment, relatively large tagged beads, from which the molecules of interest are cleaved in a series of reactions, are used. In this method, the beads are 50 to 500 μm in diameter, with capacities equivalent to 100 to 500 pmol of molecule per bead. The library is divided into about 100 pools, each containing about 100,000 beads. A certain percentage, about 25% of the molecule of interest is cleaved from the pool.

The cleaved pool is then tested in a competition or functional assay. One identifies the pool with the highest activity and then retrieves the remainder of the original pool and aliquots the remainder into 100 pools of about 1000 beads per pool. The process is repeated until one has a single bead, from which one reads the tag and identifies the compound of interest.

EXAMPLES

The following examples are included for the purpose of illustrating the invention and are not intended to limit the scope of the invention in any manner.

Example 1

Solution Phase Synthesis of 4-Thiazolidinones

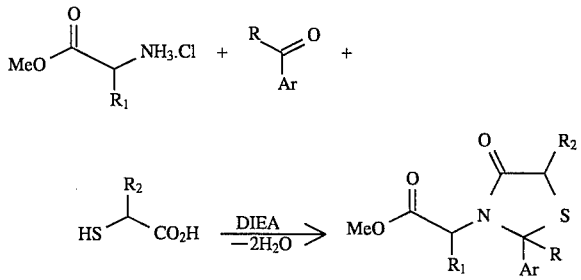

R=H, Me
$R_1$=H, Me, iPr, $CH_2Ph$
$R_2$=H, Me
Ar=Ph, MePh, Pyridine

A mixture of the nitrogen source, carboxyl source, thiol, and base in benzene (sufficient to produce a 10 mmol solution based on nitrogen source) was heated at reflux for about 18 hours with azeotropic removal of water being performed with a Dean-Stark trap. All reactions generated the theoretical amount of water within several hours but the reaction was nevertheless allowed to proceed overnight. The reaction mixture was partitioned between water and ethyl acetate. The combined organic phase was washed with saturated aqueous sodium bicarbonate and 1N aqueous hydrochloric acid, dried over magnesium sulfate, and concentrated in vacuo to yield the desired thiazolidinone esters. The thiazolidinone esters were generally colorless oils which slowly solidified upon standing. The free acid form of the thiazolidinone esters were prepared by base hydrolysis. The yields obtained from an one-pot, three component condensation reaction are reported in Table 1.

TABLE 1

Yields of thiazolidinones formed from a solution-phase reaction

| Amino Acid (eq)[1] | Aldehyde (eq)[2] | Thiol (eq)[3] | Base (eq) | Yield[4] | Yield[5] |
|---|---|---|---|---|---|
| Gly (1.0) | p-Tol (1.1) | MA (1.2) | DIEA (1.3) | 58 | 100 |
| Gly (1.0) | o-Tol (1.1) | MA (1.2) | DIEA (1.3) | 42 | 92 |
| Ala (1.0) | Benz (1.1) | MA (1.2) | DIEA (1.2) | 38 | 82 |
| Gly (1.0) | Benz (1.1) | TL (1.2) | DIEA (1.2) | 92 | 97 |
| Gly (1.0) | m-Tol (1.1) | MA (1.2) | DIEA (1.2) | 32 | 91 |
| Gly (1.0) | 3-Pyr (1.1) | MA (1.2) | DIEA (1.2) | 85 | 55 |
| Val (1.0) | Benz (1.1) | MA (1.2) | DIEA (1.3) | 14 | 99 |
| Phe (1.0) | Benz (1.1) | MA (1.2) | DIEA (1.6) | 6 | ND |
| Gly (1.0) | Aceto (2.0) | MA (3.0) | DIEA (1.4) | 42 | 90 |
| Ala (1.0) | Benz (2.0) | MA (3.0) | DIEA (1.6) | 82 | ND |
| Val (1.0) | Benz (2.2) | MA (3.7) | DIEA (1.7) | 68 | ND |
| Phe (1.0) | Benz (2.2) | MA (3.7) | DIEA (1.7) | 88 | ND |
| Val (1.0) | Benz (2.2) | MA (3.7) | DIEA (4.1) | 4 | ND |
| Phe (1.0) | Benz (2.2) | MA (3.7) | DIEA (4.1) | 27 | ND |
| Gly (1.0) | Benz (2.0) | MA (3.0) | DIEA (1.3) | 85 | 60 |
| NH$_3$ (1.0) | Benz (1.0) | MA (1.5) | — | 63 | ND |
| Gly (1.0) | Benz (2.0) | MP (3.0) | DIEA (1.3) | 40 | 93 |
| Gly (1.0) | 3-Pyr (2.0) | MA (3.0) | DIEA (1.3) | 85 | ND |
| b-Ala (1.0) | Benz (2.0) | MA (3.0) | DIEA (1.3) | 91 | 94 |

[1]The methyl ester hydrochloride salt of each amino acid was used, except for β-Ala, where the ethyl ester was used and for NH$_3$, where (NH$_3$)$_2$CO$_3$ was used.
[2]"p-Tol" is p-tolualdehyde; "m-Tol" is m-tolualdehyde; "o-Tol" is o-tolualdehyde; "Benz" is benzaldehyde; "3-Pyr" is 3-pyridinecarboxaldehyde; "Aceto" is acetophenone.
[3]"MA" is mercaptoacetic acid; "TL" is thiolactic acid; "MP" is mercaptopropionic acid.
[4]Yield for the ester after chromatography on silica gel.
[5]Yield after chromatography of the acid generated via base hydrolysis of the ester.

Example 2

Solid Phase Synthesis of 4-Thiazolidinones

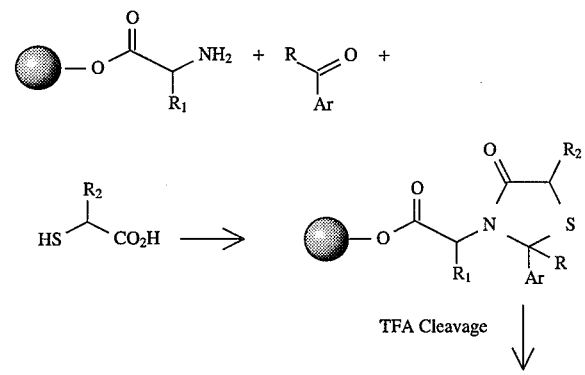

TFA Cleavage

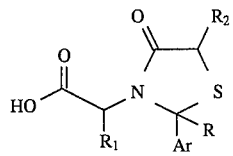

R=H, Me
R$_1$=H, Me, iPr, CH$_2$PH
R$_2$=H, Me
Ar=Ph, MePh, Pyridine.

A mixture of the nitrogen source which had been immobilized on a resin, preferably a polystyrene-based resin with an acid cleavable linker (e.g., TentaGel AC), carbonyl component (0.215M, ≈10–20 equivalents), thiol component(0.5M, ≈20–40 equivalents), and optionally, an exogenous base, in acetonitrile (sufficient to produce a 10 mmol solution based on nitrogen source) was heated for 2 hours at 70° C. with 3 Å molecular sieves being present as intact beads. The reaction was performed in glass vials with a screw top closure. No attempts were made to exclude oxygen. The reaction mixture was then transferred via pipette to a disposable filter tube and was washed extensively with CH$_2$Cl$_2$, DMF, and MeOH. The thiazolidinone product was cleaved from the resin in the filter tube with 50% TFA/CH$_2$Cl$_2$ for 30–60 minutes. Control experiments with the authentic standards prepared in solution demonstrated that all the compounds were stable to the TFA treatment.

The solutions containing the thiazolidinones (or metathiazanones) were evaporated to dryness and the residue weighed and taken up in ACN/H$_2$O for analysis by HPLC. FIGS. 8, 9, 10, and 11 show representative HPLC traces for various solid-state condensations and the corresponding solution phase reaction. In general, co-injection of an authentic standard with the crude thiazolidinone or metathiazanone showing a single sharp peak was taken as proof of identity.

The observed purities measured via HPLC analysis obtained from one-pot, three component condensation reactions using valine as the amine component, different resins and linkers are reported in Table 2 below. The solid phase synthesis of all the thiazolidinones represented in Table 1 was carried out using the methods described above.

TABLE 2

Yields of thiazolidinones formed from a solid-phase reaction

| Time (h) | Resin/Linker | Purity (%)[6] | Purity (%)[7] |
|---|---|---|---|
| 0.5 | PS/PAC | 16 | N.D. |
| 1.0 | PS/PAC | 20 | N.D. |
| 2.0 | PS/PAC | 20 | 25 |
| 3.0 | PS/PAC | 24 | N.D. |
| 4.0 | PS/PAC | 32 | 39 |
| 2.0 | TentaGel/AC | 47 | N.D. |
| 2.0 | PS/Sasrin | 36 | N.D. |
| 2.0 | PS/Sasrin | N.D. | 13[8] |

[6]One pot reaction, 0.25 mM benzaldehyde, 0.5M mercaptoacetic acid. Percent purity is for both diastereomers combined.
[7]Resin washed and fresh reagents added every 60 minutes.
[8]Stepwise reaction: imine formation for 1 hour, followed by washing and addition of mercaptoacetic acid for an additional 1 hour.

Example 3

Effect of Reagent Concentration

Commercially available Fmoc-Val-AC-TentaGel (Rapp Polymere, Tübingen, Germany, 400 mg, 0.26 mmol/g loading) was deprotected by suspending the resin in 30% piperidine/DMF for 30 min. The resin was washed (3×5 mL DMF, 3×5 mL CH$_2$Cl$_2$), and dried under vacuum for 1 hour. The dried resin was partitioned (roughly 40 mg of resin per vial) into 8 4-mL vials equipped with a screw top closure. ACN (2 mL) and 3 Å molecular sieves (20–30 pellets) were added to each vial. Benzaldehyde (PhCHO) and mercaptoacetic acid (thiol) were added to each vial to generate the following concentration array: 0.25M PhCHO, 0.5M thiol; 0.25M PhCHO, 1.0M thiol; 0.25M PhCHO, 2.0M thiol; 0.5M PhCHO, 0.5M thiol; 0.5M PhCHO, 1.0M thiol; 0.5M PhCHO, 2.0M thiol; 1.0M PhCHO, 1.0M thiol; 1.0M PhCHO, 2.0M thiol. The vials were heated to 70° C. for 2 hours by placing them into a dry heating block (VWR Scientific, San Francisco, Calif.). The vials were cooled to room temperature and the resin was transferred to disposable filter tubes and washed extensively (3×5 mL CH$_2$Cl$_2$, 3×5 mL DMF, 3×5 mL CH$_2$Cl$_2$, 3×5 mL MeOH, 3×5 mL CH$_2$Cl$_2$). The thiazolidinones were then cleaved from the resin by suspending the resin in 50% TFA/CH$_2$Cl$_2$ for 45 minutes, followed by filtration. The TFA solution was removed under reduced pressure and the resultant thiazolidinones dissolved in 2 mL of 50% ACN/H$_2$O for analysis by HPLC. The samples were injected onto a 4.6 mm×25 cm C$_{18}$ reverse phase HPLC column with the following gradient: 20% B for 1 minute, then to 70% B over 20 minutes, 1 mL/min flow rate, A: H$_2$O containing 0.1% TFA, B: ACN containing 0.1% TFA. UV detection at 220 nm. The data indicated that with the low concentration conditions (0.25M PhCHO, 0.5M thiol), roughly 47% of the material observed by HPLC were the two product diastereomers, whereas under higher concentration conditions (1.0M PhCHO, 2.0M thiol), the two products comprised roughly 81% of the material.

Example 4

Stepwise Synthesis of 4-Thiazolidinones

Figure 12:
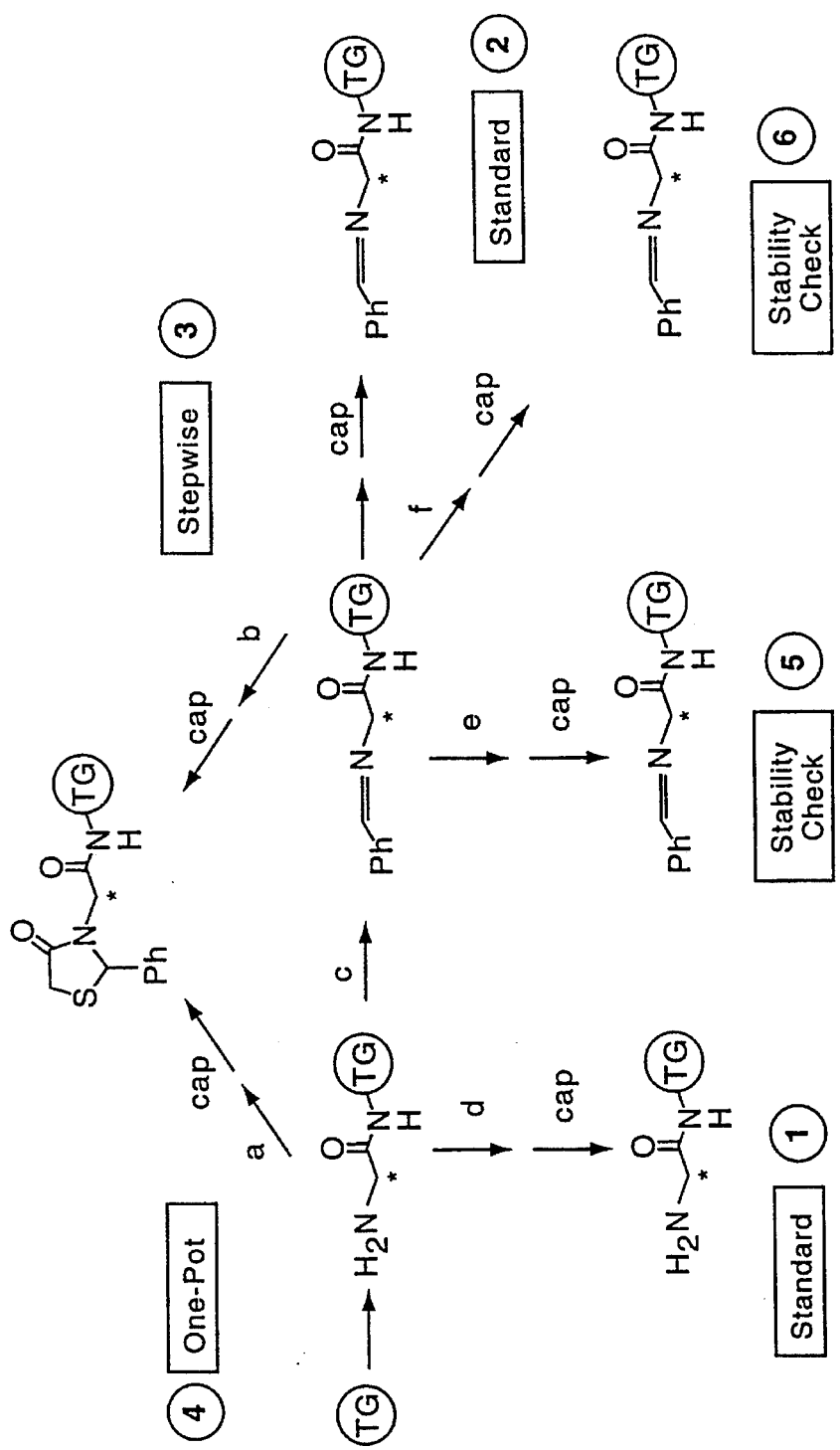
FIG. 12 provides a schematic drawing illustrating a reaction sequence carried out to demonstrate the practicality of a stepwise condensation reaction and the stability of various intermediates.
Figures 13A, 13B, 13C, 13D:
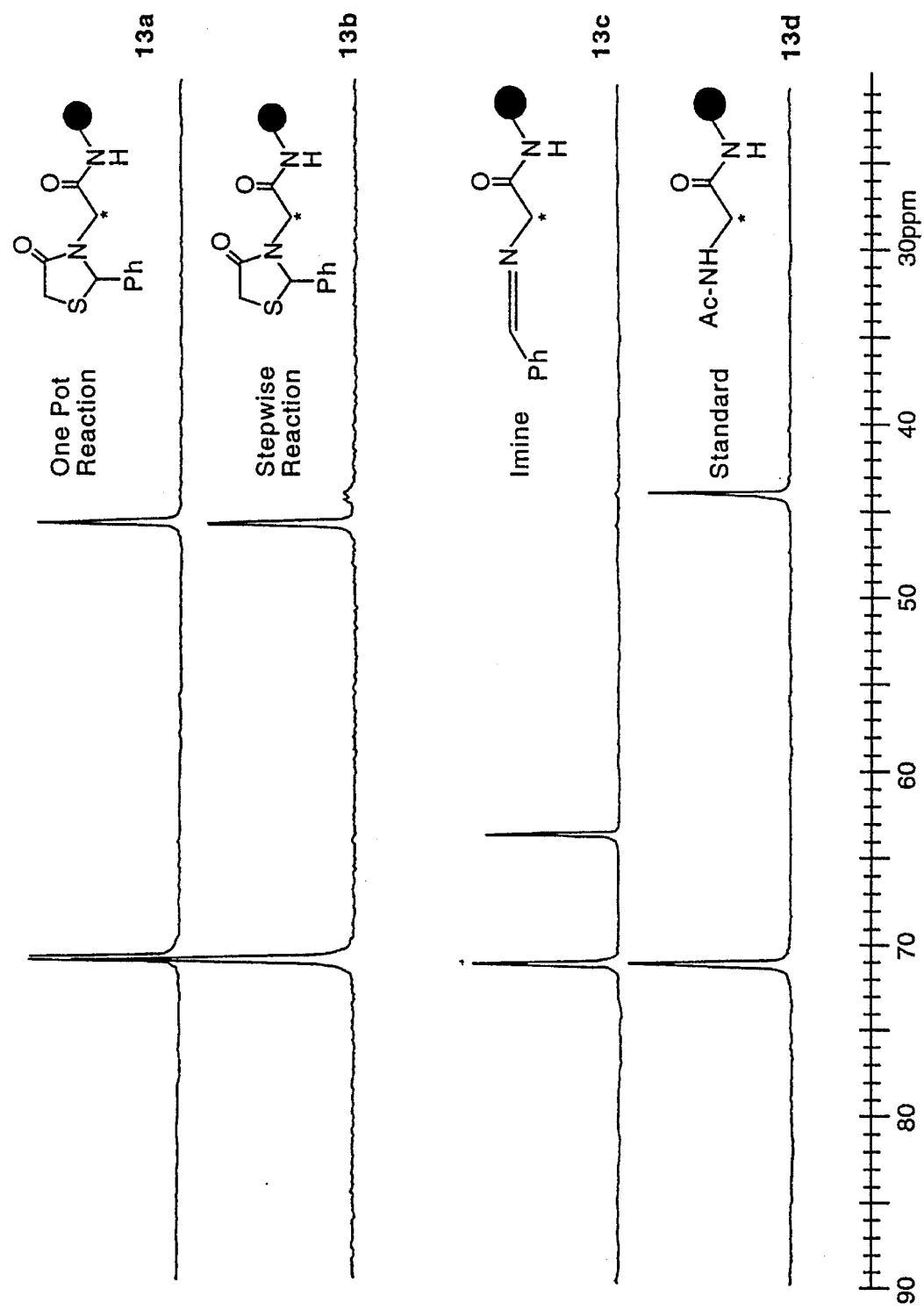
FIG. 13 illustrates the use of $^{13}$C NMR to monitor the reactions set forth in FIG. 12. Panel D shows the $^{13}$C NMR spectrum of N-acetylated support-bound glycine which has been labeled with a $^{13}$C-atom at the position alpha to the carbonyl. Panel C shows the $^{13}$C NMR spectrum of the support-bound labeled imine produced by the reaction of support-bound labeled glycine with benzaldehyde, followed by treatment with acetic anhydride and pyridine. Panel B shows the $^{13}$C NMR spectrum of the labeled thiazolidinone produced by the reaction of support-bound labeled imine with mercaptoacetic acid, followed by treatment with acetic anhydide and pyridine. Panel A shows the $^{13}$C NMR spectrum of the product of the one-step condensation reaction of support-bound labeled glycine with benzaldehyde and mercaptoacetic acid, followed by treatment with acetic anhydride and pyridine.

To explore the stepwise synthesis of 4-thiazolidinones, the reaction sequence shown in FIG. 12 was attempted. All reactions were carried out in in acetonitrile in the presence of 3 Å molecular sieves at 70° C. for one hour. The amine component was prepared by coupling glycine to TentaGel NH$_2$ resin. A portion of the material was subjected to a one-pot condensation reaction with benzaldehyde (0.75M) and α-mercaptoacetic acid (2M). The HPLC trace for this reaction is shown in Panel A of FIG. 13. A second portion of the immobilized glycine was treated with acetonitrile and then capped by treatment with acetic anhydride and pyridine in methylene chloride. The HPLC trace for this reaction is shown in Panel D of FIG. 13 and Panel D of 14.

Figures 14A, 14B, 14C, 14D:
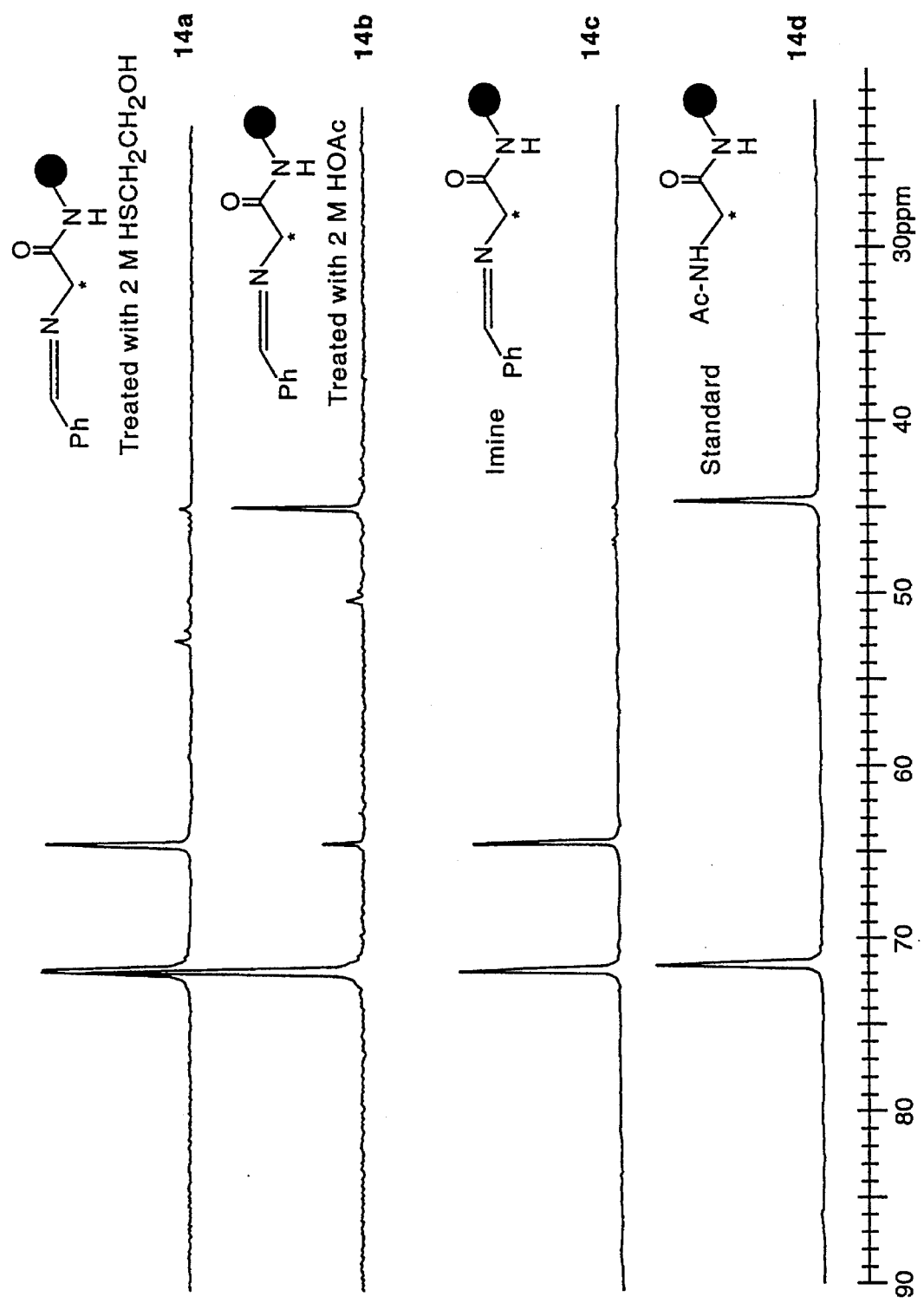
FIG. 14 further illustrates the use of $^{13}$C NMR to monitor the reactions set forth in FIG. 12. Panel D shows the $^{13}$C NMR spectrum of N-acetylated support-bound glycine which has been labeled with a $^{13}$C-atom at the position alpha to the carbonyl. Panel C shows the $^{13}$C NMR spectrum of the support-bound labeled imine produced by the reaction of support-bound labeled glycine with benzaldehyde, followed by treatment with acetic anhydride and pyridine. Panel B shows the $^{13}$C NMR spectrum of the labeled imine produced by reaction of the support-bound labeled imine and benzaldehyde, followed by treatment with 2M acetic acid and then with acetic anhydride and pyridine. Panel A shows the $^{13}$C NMR spectrum of the labeled imine produced by reaction of the support-bound labeled imine and benzaldehyde, followed by treatment with 2M 2-mercaptoethanol and then with acetic anhydride and pyridine.

A final portion of the immobilized glycine was treated with benzaldehyde (0.75M) to yield the corresponding imine. The support bound imine was divided into four components as shown in FIG. 12. To prepare a standard sample of the support bound imine for analytical purposes, one portion of the imine was capped by treatment with acetic anhydride and pyridine in methylene chloride. The HPLC trace for this reaction is shown in Panel C of FIG. 13 and Panel C of FIG. 14. The absence of N-acetylglycine in the HPLC traces indicates that the imine is stable to acetic anhydride and that complete conversion to imine had taken place within one hour.

To analyze the stability of the imine to acid treatment, one portion of the imine was treated with 2M acetic acid and then capped by treatment with acetic anhydride and pyridine in methylene chloride. The HPLC trace for this reaction is shown in Panel B of FIG. 14. To analyze the stability of the imine to treatment with a thiol group, (in the absence of a carboxylic group), one portion of the imine was treated with 2-mercaptoethanol (2M). The HPLC trace for this reaction is shown in Panel A of FIG. 14. These studies show that the support-bound imine is stable to treatment with a thiol group and partially degrades upon extended exposure to acid.

Finally, to examine the ability of the support-bound imine to react with a thiol component, the imine was treated with α-mercapacetic acid (2M). The HPLC trace for this reaction is shown in Panel B of FIG. 13. Significantly, this HPLC trace is equivalent to that found for the one-pot condensation indicating that the support-bound imine is stable to washing and handling, and thus is amenable to the stepwise reaction scheme illustrated in FIG. 5.

Example 5

Synthesis of Thiazolidinones on a Resin with a Photocleavable Linker

Commercially available H$_2$N-S-TentaGel (Rapp Polymere, Tübingen, Germany, 1 g, 0.30 mmol/g loading) was washed with DMF and treated with 3 mL of a 0.15M solution of OBt-activated Fmoc-photolinker (prepared from 310 mg of Fmoc-linker, 92 mg of HOBt, 95 μL of DIC in 3 mL of DMF) for 1.5 hour. Ninhydrin test indicated a complete reaction had taken place. The resin was washed with DMF and CH$_2$Cl$_2$, and was then capped by treatment with 20% Ac$_2$O and 30% pyridine in 50% CH$_2$Cl$_2$ for 30 minutes. The resin was washed (3×5 mL DMF, 3×5 mL CH$_2$Cl$_2$), and dried under vacuum for 1 hour. A portion of the resin (200 mg) was deprotected with 30% piperidine/DMF for 30 minutes and then washed with DMF. A 0.5M solution of Fmoc-Glycine symmetrical anhydride (prepared from 182 mg of Fmoc-Gly-OH and 50 μL of DIC in 0.6 mL of DMF) was coupled to the resin for 1 hour, by which time ninhydrin had revealed that a complete reaction had taken place. The resin was washed and capped as above for 30 minutes. Deprotection with piperidine, washing and drying as above gave roughly 150 mg of dry resin. The dried resin was partitioned (roughly 40 mg of resin per vial) into 2 4-mL vials equipped with a screw top closure. ACN (2 mL) and 3 Å molecular sieves (20–30 pellets) were added to each vial. Benzaldehyde (152 μL) and mercaptoacetic acid (300 μL) was added to the first vial whereas 2,4-dimethoxybenzaldehyde (250 mg) and mercaptoacetic acid (300 μL) was added to the second vial. Both vials were heated to 70° C. for 2 hours. The vials were cooled to room temperature and the resin was transferred to disposable filter tubes and washed extensively (3×5 mL CH$_2$Cl$_2$, 3×5 mL DMF, 3×5 mL CH$_2$Cl$_2$, 3×5 mL MeOH, 3×5 mL CH$_2$Cl$_2$, 3×5 mL Et$_2$O).

Roughly 2 mg of each of the two types of resin were placed in plastic centrifuge tubes equipped with 0.22 μm membrane filters (Ultrafree-MC Filter Units from Millipore, Bedford, Mass.) and were suspended in 100 μL of pH 7.4 PBS buffer. Photolysis were conducted with a 500 W Hg ARC lamp fitted with a 350–450 nm dichroic mirror at a 10 mW/cm$^2$ power level measured at 365 nm. The samples were irradiated from above for various times and the samples were gently mixed during photolysis with an orbital shaker table. After photolysis the samples centrifuged and the filtrate collected. The samples were washed with 100 μL of 50% ACN/H$_2$O and again centrifuged. The collected filtrates from each sample were analyzed by HPLC for the presence of thiazolidinone. See FIG. 15. The data indicated that both the thiazolidinones were produced in high purity on the resin and that they were stable to the photolysis conditions.

Example 6

$^{13}$C-NMR Experiments: Monitoring Reaction Progress and Stability

A. Preparation of Double-Labeled Thiazolidinone

H$_2$N-S-TentaGel (500 mg) was elaborated in analogy to example 2 with Fmoc-Gly-OH labeled at the α-carbon with $^{13}$C (2-$^{13}$C, 99% from Cambridge Isotope Laboratories, Inc., Andover, Mass.). The resin was capped with Ac$_2$O as above, deprotected with piperidine, and the Fmoc-photolinker coupled as its OBt-activated ester. The resin was again capped, deprotected, and reacted with unlabeled Fmoc-Glycine-OH as its anhydride. An additional round of capping and deprotection generated the free amine resin. Reaction with 0.75M PhCHO labeled at the carbonyl (carbonyl-$^{13}$C, 99% from Cambridge Isotope Laboratories, Inc., Andover, Mass.) and 2.0M mercaptoacetic acid in ACN containing 3 Å molecular sieves for 2 hours at 70 C. generated the double labeled thiazolidinone resin. The resin was washed extensively (3×5 mL CH$_2$Cl$_2$, 3×5 mL DMF, 3×5 mL CH$_2$Cl$_2$, 3×5 mL MeOH, 3×5 mL CH$_2$Cl$_2$, 3×5 mL Et$_2$O) and dried under vacuum.

B. TFA Stability Studies

A portion (20 mg) of the resin was treated with 95% TFA/5% H$_2$O for 1 hour, followed by washing with CH$_2$Cl$_2$, MeOH, and Et$_2$O. Gel $^{13}$C NMR analysis of the resin indicated no loss of thiazolidinone, as evidenced by relative integration of the two labeled carbons. See Panel B, FIG. 2. Any destruction of either the photolinker or thiazolidinone would be expected to result in the integration of the benzylic carbon to decrease. This experiment demonstrated that both the photolinker and thiazolidinone were stable to TFA treatment.

C. DNA Synthesis Stability Studies

A portion (20 mg) of the resin was loaded into a standard DNA synthesis cartridge and subjected to 40 cycles of DNA synthesis with A, C, and T nucleosides employed as their phosphoramidites followed by iodine oxidation after every cycle. "Mock" dimethoxytrityl (DMT) removal was accomplished by treating the resin with 2% TFA/CH$_2$Cl$_2$ at the start of every cycle. The resin was removed from the cartridge, washed with DMF, and was analyzed by gel $^{13}$C NMR spectroscopy. See Panel A, FIG. 2. The spectrum obtained revealed little or no destruction of either the photolinker or thiazolidinone molecules. A portion (2 mg) of the resin was also photolyzed as above for 3 h in pH 7.4 PBS buffer and the liberated thiazolidinone analyzed by HPLC. See Panel A, FIG. 3 and FIG. 4. The data revealed that the thiazolidinone was released in high purity and that both the photolinker and thiazolidinone were not significantly altered upon treatment with standard DNA synthesis reagents.

Example 7

Preparation of Thiazolidinone Library

Fmoc-RAM-TentaGel resin (500 mg, 0.26 mmol/g loading) was deprotected with 30% piperidine/DMF for 30 minutes, followed by washing with DMF. Fmoc-Ala-OH was coupled to the support as its symmetrical anhydride (prepared from 802 mg of Fmoc-Ala-OH and 200 µL of DIC in 2.5 mL of DMF) at a concentration of 0.5M for 1 hour. The resin was washed with DMF and CH$_2$Cl$_2$ and was capped with 20% Ac$_2$O/30% pyridine in 50% CH$_2$Cl$_2$ for 30 minutes. The resin was washed (CH$_2$Cl$_2$ and MeOH) and dried under vacuum for 1 hour. The resin was mixed with Fmoc-Gly-AC-TentaGel (643 mg, 0.28 mmol/g loading), Fmoc-Ala-AC-TentaGel (615 mg, 0.21 mmol/g loading), and Fmoc-Gly-RAM-TentaGel (566 mg, 0.23 mmol/g loading). The mixture of resins was thoroughly mixed by vortexing the resins together successively in CH$_2$Cl$_2$ and MeOH. The resin was then dried under vacuum for 1 hour to give roughly a 1:1:1:1 mixture of Fmoc-Gly-amide-support, Fmoc-Gly-acid-support, Fmoc-Ala-amide-support, and Fmoc-Ala-acid-support.

Figure 16:
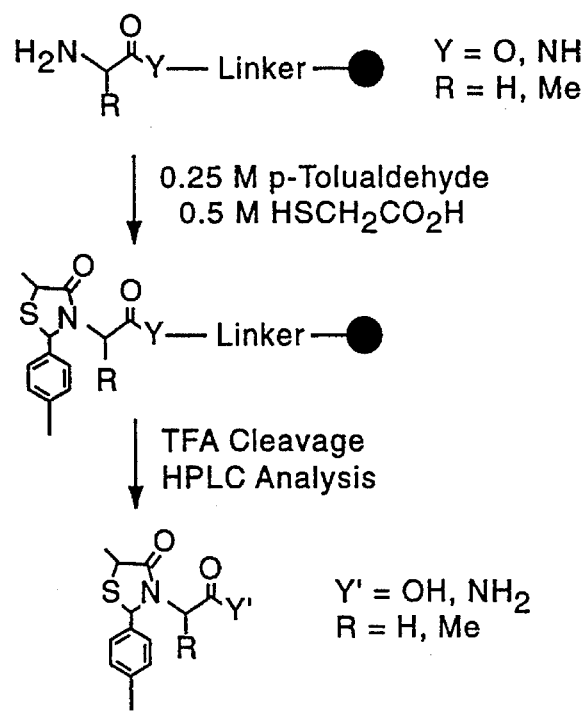
FIG. 16 shows a HPLC trace and reaction scheme for the preparation of a library of thiazolidinones resulting from the reaction of p-tolualdehyde, mercaptoacetic acid, and various amino acids.
Figure 16:
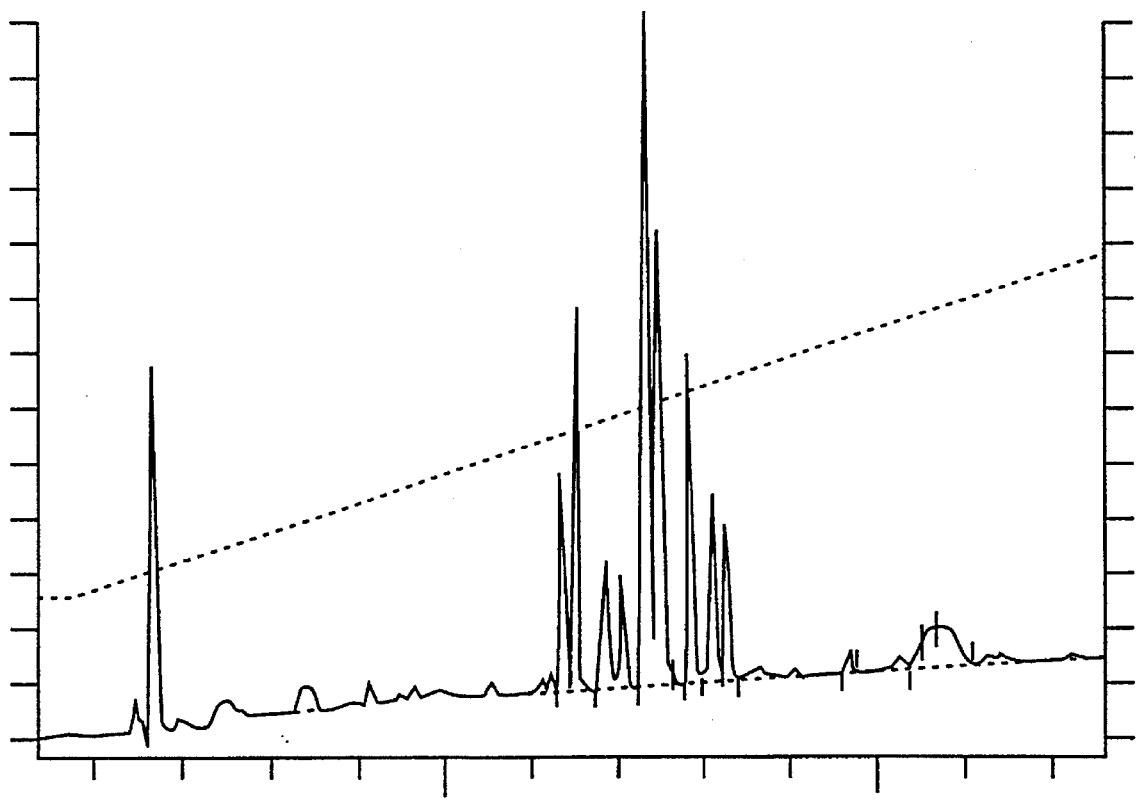

A portion of the above resin (425 mg) was deprotected with 30% piperidine/CH$_2$Cl$_2$ for 30 minutes, followed by washing with DMF and CH$_2$Cl$_2$. The resin was dried under vacuum for 2 hour and then transferred to a 4-mL vial. A mixture of ACN (2 mL), 3 Å molecular sieve (20–30 pellets), p-tolualdehyde (59 µL), and thiolactic acid (89 µL) was added and the vial heated to 70° C. for 2 hours. The vial was cooled to room temperature and the resin was transferred to disposable filter tubes and washed extensively (3×5 mL CH$_2$Cl$_2$, 3×5 mL DMF, 3×5 mL CH$_2$Cl$_2$, 3×5 mL MeOH, 3×5 mL CH$_2$Cl$_2$). The thiazolidinones were cleaved from the support with 50% TFA/CH$_2$Cl$_2$ for 1 hour, followed by filtration. The TFA solution was removed under reduced pressure and the resultant thiazolidinones dissolved in 2 mL of 50% ACN/H$_2$O for analysis by HPLC. The HPLC profile is illustrated in FIG. 16.

Example 8

Preparation of a Thiazolidinone Derivative

Commercially available Fmoc-Gly-AC-TentaGel (Rapp Polymere, Tübingen, Germany, 200 mg, 0.26 mmol/g loading) was deprotected with 30% piperidine/DMF for 30 minutes, washed with DMF and CH$_2$Cl$_2$ and dried under vacuum for 2 hours. The dried resin was placed into a 4-mL vial equipped with a screw top closure. A mixture of ACN (2 mL), 3 Å molecular sieves (20–30 pellets), benzaldehyde (160 µL of carbonyl-$^{13}$C labeled, Cambridge Isotope laboratories, Inc., Andover, Mass.) and mercaptoacetic acid (300 µL) was added to the vial and then heated to 70° C. for 2 hours. The vial was cooled to room temperature and the resin was transferred to disposable filter tubes and washed extensively (3×5 mL CH$_2$Cl$_2$, 3×5 mL DMF, 3×5 mL CH$_2$Cl$_2$, 3×5 mL MeOH, 3×5 mL CH$_2$Cl$_2$, 3×5 mL Et$_2$O).

Figures 17A, 17B:
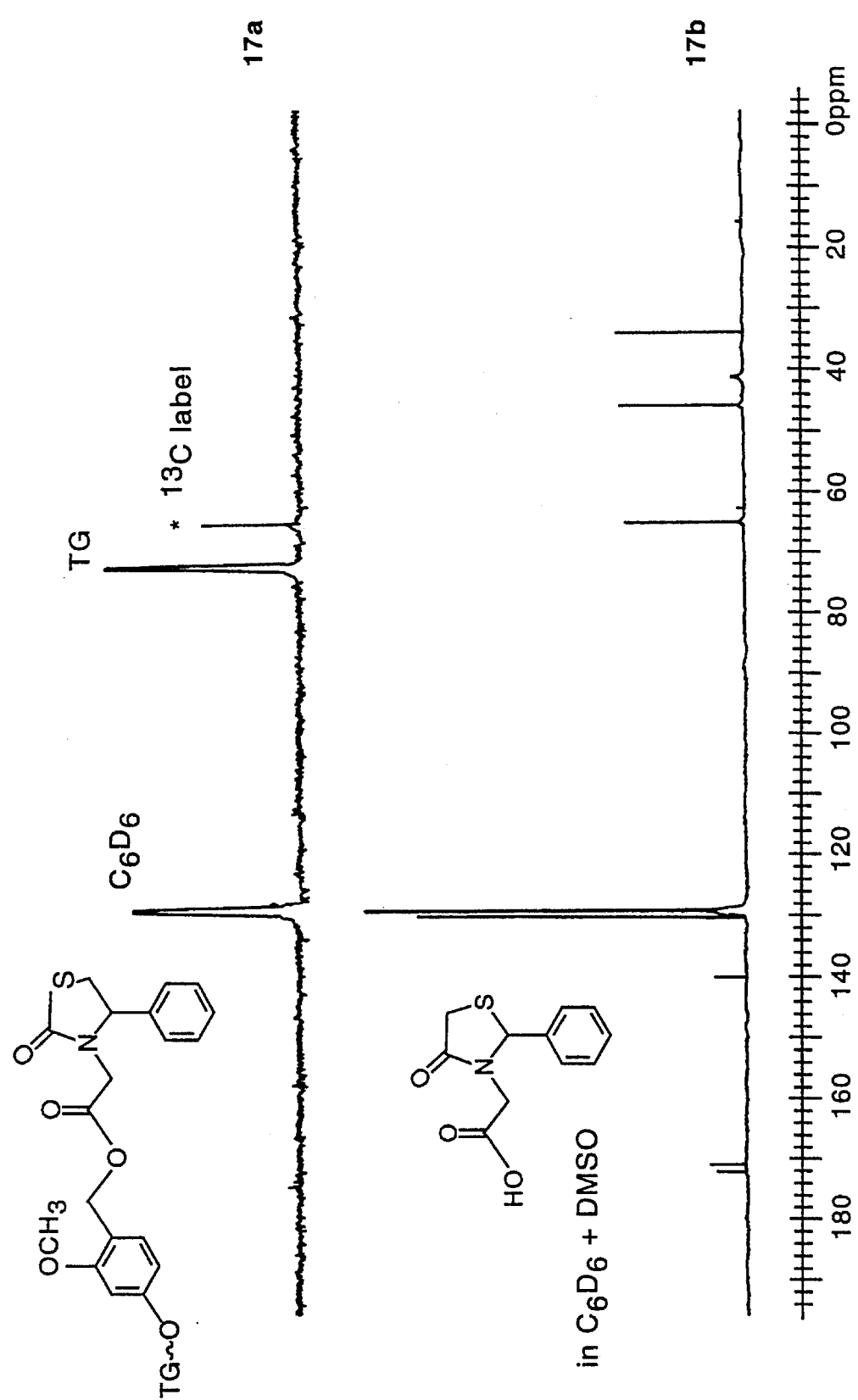
FIG. 17 illustrates the preparation of a thiazolidinone derivative. Specifically, Panel A shows the gel $^{13}$C NMR spectrum of a labeled support-bound thiazolidinone prepared from benzaldehyde, glycine, and mercaptoacetic acid with the $^{13}$C label indicated with a "*". Panel B shows a conventional $^{13}$C NMR spectrum of the corresponding unlabeled thiazolidinone in solution. Panel C shows the gel $^{13}$C NMR spectrum of the product of the reaction of the labeled support-bound thiazolidinone with 3-chloroperoxybenzoic acid. Panel D shows a conventional $^{13}$C NMR spectrum of the corresponding unlabeled sulfone in solution.
Figures 17C, 17D:
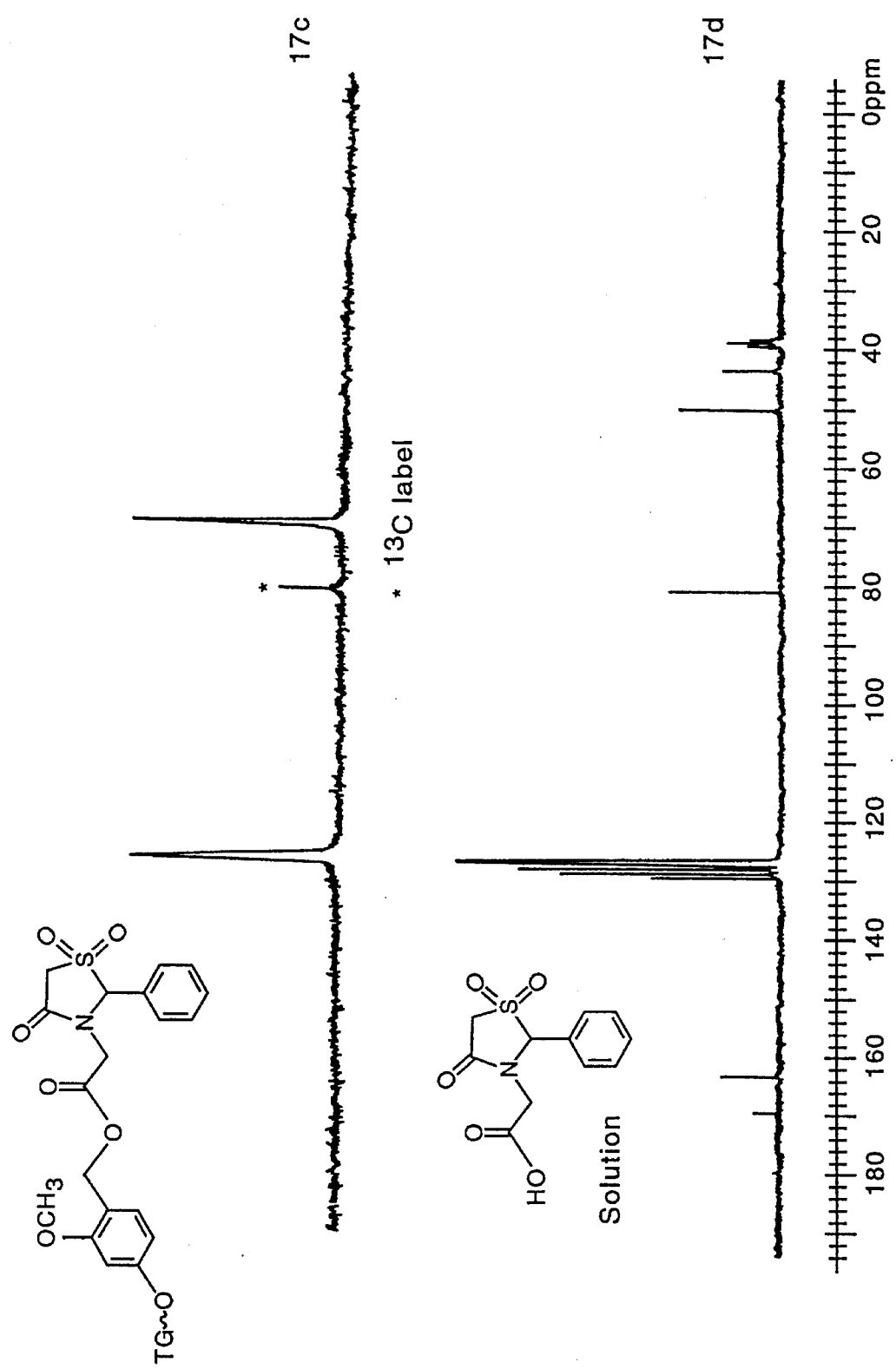

Gel $^{13}$C NMR spectroscopic analysis revealed a single peak at roughly 63 ppm (see Panel A of FIG. 17), which matched the chemical shift for the benzylic carbon when measured via conventional $^{13}$C NMR (see Panel B of FIG. 17). A portion of the resin (20 mg) was treated with a 0.25M solution of 3-chloroperoxybenzoic acid in CH$_2$Cl$_2$ for 5 hours at room temperature, followed by washing with CH$_2$Cl$_2$, DMF, and MeOH. Gel $^{13}$C NMR spectroscopic analysis (see Panel C of FIG. 17) indicated that complete conversion to the corresponding sulfone had taken place, as evidenced by the shift of the benzylic carbon resonance to roughly 82 PPM. This new resonance matched the resonance for the benzylic carbon measured in solution on a authentic sample of the sulfone (see Panel D of FIG. 15). HPLC analysis of the material cleaved from the resin upon treatment with 50% TFA/CH$_2$Cl$_2$ indicated complete conversion to the sulfone product had taken place.

The above description is illustrative and not restrictive. Many variations of the invention will become apparent to those of skill in the art upon review of this disclosure.

Merely by way of example a wide variety of process times, reaction temperatures, and other reaction conditions may be utilized, as well as a different ordering of certain processing steps. The scope of the invention should, therefore, be determined not with reference to the above description, but instead should be determined with reference to the appended claims along with their full scope of equivalents. Although certain embodiments and examples have been used to describe the invention, changes may be made to those embodiments and examples without departing from the scope of the following claims or spirit of the invention.

What is claimed is:

1. A library of 4-thiazolidinones, metathiazinones, or derivatives thereof comprising a plurality of different compounds, each compound covalently linked to a solid support, wherein each of said compounds comprises at least one 4-thiazolidinone group, metathiazinone group, or a group derived from a 4-thiazolidinone group or metathiazinone group which group is prepared by the method which comprises:

(a) on a surface of a solid support, providing an amine component having the formula:

wherein R is selected from the group consisting of alkyl, alkoxy, amino, aryl, aryloxy, heteroaryl, and arylalkyl or salts thereof;

(b) treating the amine component with a carbonyl component having a formula:

wherein $R^3$ is hydrogen and $R^4$ is selected from the groups consisting of consisting of alkyl, aryl, heteroaryl, and arylalkyl;

and a thiol component having a formula:

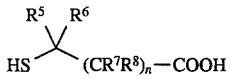

wherein $R^5$, $R^6$, $R^7$, and $R^8$ are independently selected from the groups consisting of hydrogen, alkyl, alkoxy, aryl, aryloxy, heteroaryl, carboxyl, carboxyalkyl, carboxyaryl, and arylalkyl and n is either 0 or 1 wherein n being 0 represents a valence bond;

under conditions effective to cyclize the components and form a solid support-bound 4-thiazolidinone, metathiazinone, or a derivative thereof and provided that at least one of the following conditions is satisfied:
  i) at least two different amine components are used
  ii) at least two different carbonyl components are used;
  iii) at least two different thiol components are used; or
  iv) at least two different sets of conditions effective to cyclize the components are used.

2. The library of claim 1, wherein each compound of said plurality of different compounds is covalently linked to the same solid support.

3. The library of claim 2, wherein the solid support is glass.

4. The library of claim 1, wherein each compound of said plurality of different compounds is covalently linked to a different solid support.

5. The library of claim 4, wherein the solid support is a bead.

6. The library of claim 5, wherein the beads further comprise a linker and wherein one end of the linker is attached to the amino component.

7. The library of claim 6, wherein the linker is cleavable.

8. The library of claim 5, wherein each of the beads further comprises a support-bound identifier tag, wherein the tag identifies a molecule attached thereto.

9. The library of claim 8, wherein the tag is an oligonucleotide.

10. The library of claim 1, wherein n is 0.

11. A library of 4-thiazolidinones, metathiazinones, or derivatives thereof comprising a plurality of different compounds, each compound covalently linked to a solid support, wherein each of said compounds comprises at least one 4-thiazolidinone group, metathiazinone group, or a group derived from a 4-thiazolidinone group or metathiazinone group which group is prepared by the method which comprises:

(a) on a surface of a solid support, providing a thiol component having a formula:

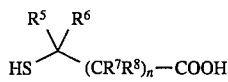

wherein $R^5$, $R^6$, $R^7$, and $R^8$ are independently selected from the groups consisting of hydrogen, alkyl, alkoxy, aryl, aryloxy, heteroaryl, carboxyl, carboxyalkyl, carboxyaryl, and arylalkyl and n is either 0 or 1 wherein n being 0 represents a valence bond;

(b) treating the thiol component with an amine component having the formula:

wherein R is selected from the group consisting of hydrogen, alkyl, alkoxy, amino, aryl, aryloxy, heteroaryl, and arylalkyl or salts thereof, and a carbonyl component having a formula:

wherein $R^3$ is hydrogen and $R^4$ is selected from the groups consisting of alkyl, aryl, heteroaryl, and arylalkyl;

under conditions effective to cyclize the components and form a solid support-bound 4-thiazolidinone, metathiazinone, or a derivative thereof and provided that at least one of the following conditions is satisfied:
  i) at least two different amine components are used
  ii) at least two different carbonyl components are used;
  iii) at least two different thiol components are used; or
  iv) at least two different sets of conditions effective to cyclize the components are used.

* * * * *